US012696870B2

(12) United States Patent
Wanten

(10) Patent No.: US 12,696,870 B2
(45) Date of Patent: Aug. 4, 2026

(54) TOMATO VARIETY NUN 09398 TOF

(71) Applicant: Nunhems B.V., Nunhem (NL)

(72) Inventor: Pascal Wanten, Nunhem (NL)

(73) Assignee: Nunhems B.V., Nunhem (NL)

( * ) Notice: Subject to any disclaimer, the term of this patent is extended or adjusted under 35 U.S.C. 154(b) by 381 days.

(21) Appl. No.: 18/188,267

(22) Filed: Mar. 22, 2023

(65) Prior Publication Data

US 2023/0225281 A1 Jul. 20, 2023

Related U.S. Application Data

(60) Provisional application No. 63/354,496, filed on Jun. 22, 2022.

(51) Int. Cl.
A01H 6/82 (2018.01)
A01H 5/08 (2018.01)

(52) U.S. Cl.
CPC ............... A01H 6/825 (2018.05); A01H 5/08 (2013.01)

(58) Field of Classification Search
None
See application file for complete search history.

(56) References Cited

U.S. PATENT DOCUMENTS

| | | | |
|---|---|---|---|
| 6,060,648 A | 5/2000 | Heath | |
| 9,125,353 B2 | 9/2015 | De Haan et al. | |
| 10,757,906 B2 * | 9/2020 | Silvertand .............. | A01H 6/825 |
| 2002/0010953 A1 | 1/2002 | Van Vliet | |
| 2008/0222949 A1 | 9/2008 | Bissonnette et al. | |
| 2015/0126380 A1 | 5/2015 | Van Dun | |
| 2015/0245570 A1 | 9/2015 | Vogelaar et al. | |
| 2021/0112767 A1 * | 4/2021 | Schroeder .............. | A01H 6/825 |

FOREIGN PATENT DOCUMENTS

| | | |
|---|---|---|
| EP | 1057401 A1 | 12/2000 |
| EP | 1428425 A1 | 6/2004 |

OTHER PUBLICATIONS

Tiersma 2022, Fresh Plaza, Jun. 3, 2022; freshplaza.com/europe/article/9432945/we-re-fast-tracking-this-tomato-variety (Year: 2022).*
Fruit Logistica-Newsletter, "Fruit Logistica 2022—Berlin, Germany" ; thracegroup.com/gr/en/events/fruit-logistica-2022-berlin-germany-9-11-february-2022/ (Year: 2022).*
Ahuja et al, 1997, Transgenes and Genetic Stability, Chapter 13, USDA Forest Service Gen. Tech. Rep. RM-GTR-297, p. 90-100 (Year: 1997).*
Krishna et al 2016, 3 Biotech, 6:1-18 (Year: 2016).*
"DUS Test for Tomato—Solanum lycopersicum L., Calibration Manual Harmonized with Naktuinbouw and NCSS(/NARO)", Jan. 24, 2020, 73 pages.
"Fruit Logistica 2022—Berlin, Germany", Fruit Logistica-Newsletter, Apr. 5-7, 2022 , 2 pages. URL-https://www.thracegroup.com/gr/en/events/fruit-logistica-2022-berlin-germany-9-11-february-2022/.
"Guidelines for the conduct of tests for distinctness, uniformity and stability—Tomato, UPOV Code(s): SOLAN_LYC, Solanum lycopersicum L.", UPOV, International Union for the Protection of New Varieties of Plants, Geneva, TG/44/11, Revision 3, Oct. 29, 2019, 77 pages.
"Objective description of Variety: Tomato (Lycopersicon esculentum Mill.)", US Department of Agriculture, Agricultural Marketing Service, Science and Technology, Plant Variety Protection Office, Exhibit C, Dec. 2018, 9 pages.
Bhatia, et al., "Tissue Culture Studies of Tomato (Lycopersicon esculentum)", Plant Cell, Tissue and Organ Culture, vol. 78, Issue 1, Jul. 2004, pp. 1-21.
Hartz, et al., "Processing tomato production in California", University of California Agriculture and Natural Resources, Publication 7228, 1996, pp. 1-5.
Ince, et al., "Genetic Relationships Within and Between Capsicum Species", Biochemical Genetics, vol. 48, Issue 1-2, Nov. 15, 2009, pp. 83-95.
Needleman, et al., "A general method applicable to the search for similarities in the amino acid sequence of two proteins", Journal of Molecular Biology, vol. 48, Issue 3, 1970, pp. 443-453.
Nikolova, et al., "Diploidization of cucumber (Cucumis sativus L.) haploids by colchicine treatment", Acta Societas Botanicorum Poloniae, vol. 65, Issue 3-4, 1996, pp. 311-317.
Parvathaneni, et al., "Fingerprinting in Cucumber and Melon (Cucumis spp.) Genotypes Using Morphological and ISSR Markers", Journal of Crop Science and Biotechnology, vol. 14, Issue 1, Mar. 2011, pp. 39-43.
Pisanu, et al., "Yield and biometric characteristics of 9 clones selected from the population of "spinoso sardo" artichokes", ISHS Acta Horticulturae 660, V International Congress on Artichoke, Article No. 660_9, 2004, pp. 83-89.
Rice, et al., "EMBOSS: The European Molecular Biology Open Software Suite", Trends in Genetics, vol. 16, Issue 6, Jun. 1, 2000, pp. 276-277.
Robert W. Allard, "Overview of Plant Breeding", Principles of Plant Breeding, Second Edition, 1999, pp. 64-67.
Sharifova, et al., "Assessment of Genetic Diversity in Cultivated Tomato (Solanum lycopersicum L.) Genotypes Using Rapd Primers", Journal of Horticultural Research, vol. 21, Issue 1, Jul. 30, 2013, pp. 83-89.
Songstad, et al., "Genome Editing of Plants", Critical Reviews in Plant Sciences, vol. 36, Issue 1, 2017, pp. 1-23.
Strange, et al., "Fresh-Market Tomato Production in California", University of California Agriculture and Natural Resources, Publication 8017, 2000, pp. 1-8.

(Continued)

*Primary Examiner* — Brent T Page
*Assistant Examiner* — Aleksandar Radosavljevic
(74) *Attorney, Agent, or Firm* — ArentFox Schiff LLP

(57) ABSTRACT

A new and distinct tomato variety NUN 09398 TOF is disclosed, as well as seeds and plants and fruits thereof. NUN 09398 TOF is a cherry tomato variety, comprising high resistance to *Passalora fulva* Race 0 and Groups A-E, Tomato Mosaic Virus (ToMV) Strains 0, 1, 2, and 1-2, and intermediate resistance to Tomato Brown Rugose Fruit Virus (ToBRFV).

30 Claims, 1 Drawing Sheet

(56) References Cited

OTHER PUBLICATIONS

Thijmen Tiersma, "We're fast-tracking this tomato variety", Fresh Plaza, Jun. 3, 2022, 5 pages. URL—https://www.freshplaza.com/europe/article/9432945/we-re-fast-tracking-this-tomato-variety/.

Vidavsky, et al., "Tomato Breeding Lines Resistant and Tolerant to Tomato Yellow Leaf Curl Virus Issued from Lycopersicon hirsutum", Phytopathology, vol. 88, Issue 9, Sep. 1998, pp. 910-914.

Vos, et al., "AFLP: a new technique for DNA fingerprinting", Nucleic Acids Research, vol. 23, Issue 21, Nov. 11, 1995, pp. 4407-4414.

Wijnker, et al., "Hybrid recreation by reverse breeding in *Arabidopsis thaliana*", Nature Protocols, vol. 9, Issue 4, Mar. 6, 2014, pp. 761-772.

* cited by examiner

TOMATO VARIETY NUN 09398 TOF

CROSS-REFERENCE TO RELATED APPLICATION

This application claims priority to U.S. Provisional Application No. 63/354,496, filed on Jun. 22, 2022, which is hereby incorporated by reference in its entirety.

FIELD OF DISCLOSURE

The disclosure relates to the field of plant breeding, more specifically to tomato variety NUN 09398 TOF. The disclosure further relates to vegetative reproductions of tomato variety NUN 09398 TOF, methods for tissue culture of tomato variety NUN 09398 TOF, methods for regenerating a plant from such a tissue culture, and to phenotypic variants of tomato variety NUN 09398 TOF. The disclosure also relates to progeny of tomato variety NUN 09398 TOF as a parent line with plants of other varieties or parent lines.

BACKGROUND OF THE DISCLOSURE

The goal of plant breeding is to combine various desirable traits in a single variety. Such desirable traits may include greater yield, resistance to diseases, insects or other pests, tolerance to heat and drought, better agronomic quality, higher nutritional value, enhanced growth rate, and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

Tomato (*Solanum lycopersicum* and closely related species) is naturally a diploid and the basic chromosome number of the genus is x=12, most are 2n=2x=24, including the cultivated ones. It originated in the New World and has since become a major food crop.

Tomato cultivars may be grouped by maturity, i.e., the time required from planting the seed to the stage where fruit harvest can occur. Standard maturity classifications include 'early', 'midseason' or 'late-maturing'. Another classification for tomatoes is the developmental timing of fruit set. 'Determinate' plants grow foliage, then transition into a reproductive phase of flower setting, pollination and fruit development. Consequently, determinant cultivars have a large proportion of the fruit ripen within a short time frame. Growers that harvest only once in a season favor determinant type cultivars. In contrast, 'indeterminate' types grow foliage, then enter a long phase where flower and fruit development proceed along with new foliar growth. Growers that harvest the same plants multiple times favor indeterminate type cultivars.

Tomatoes can also be classified by their target markets: fresh market and processing tomatoes. Fresh-market tomatoes are primarily used for salads, salad bar, and sandwiches, and require good storage properties. On the other hand, processing tomatoes generally requires red colored and pink to red/crimson fruit flesh and higher percentage of soluble solids. Processing tomatoes can be canned whole, canned, diced or chopped, dried, roasted, pasted, puréed or concentrated, juiced, frozen, or put into ready-made dishes, for example, sauces, stews, or soups.

Worldwide production of fresh tomatoes amounted to 186.82 million tons in 2020 with China as the leading producer followed by India, Turkey, and United States (available at world-wide web tomato news/worldwide tomato production exceeds 187 million tonnes in 2020). Tomatoes are available in the United States year-round, with California and Florida being the major producers.

In response to more recent consumer demands for dietary diversity, improved flavors, high quality and yield, longer shelf life, and food concepts, tomato breeders have also expanded the range of tomato colors from red colored fruits to creamy white, lime green, yellow, green, golden, orange, and purple colored fruits. In addition, there are multi-colored varieties exemplified by mainly red fruited varieties with green shoulders, and both striped- and variegated-colored fruit. Moreover, tomato varieties with fruits that are full flesh and low in gel (i.e., intense tomatoes) have also been developed, which offers advantages to the food service and food retail industry. Intense tomato retains its juice after cutting, and maintains its texture, color, and flavor after preparation and cooking, and also reduces the cutting waste.

Furthermore, tomato breeders are continuously developing resistant varieties against viruses and other diseases. One of the contagious viruses that have affected the tomato industry is the Tomato Brown Rugose Fruit Virus (ToBRFV), characterized by fruits having yellow spots, wrinkled patches and brown scars, making them unsaleable.

SUMMARY OF THE VARIOUS ASPECTS OF THE DISCLOSURE

The disclosure provides for tomato variety NUN 09398 TOF, products thereof, and methods of using the same.

The disclosure also provides a tomato plant or part thereof having all of the physiological and morphological characteristics of tomato variety NUN 09398 TOF when grown under the same environmental conditions, wherein a representative sample of seed has been deposited under Accession Number NCIMB 44028.

Tomato variety NUN 09398 TOF is a flavorful cherry tomato variety for the fresh market with intermediate resistance to Tomato Brown Fruit Rugose Virus (ToBRFV). The fruits are sweet with high Brix level between 7.6° to 9.2° and offer a unique balance of sweet taste, texture, and firmness of the skin.

The plant of tomato variety NUN 09398 TOF is characterized as generative and open plant with average vigor. Tomato variety NUN 09398 TOF is an early maturing variety, high yielding, and produces high quality cherry tomatoes year-round with long shelf life. This sweet cherry tomato grows on a long and flat cluster with a perfect fish bone shape and is pruning on 14 with long trusses with strong green parts. The variety is suitable for growing as traditional and lighted crops or heated greenhouse.

In another aspect, the plant of tomato variety NUN 09398 TOF or a progeny thereof comprises high resistance to *Passalora fulva* Race 0 and Groups A-E and Tomato Mosaic Virus (ToMV) Strains 0, 1, 2, and 1-2, measured according to UPOV standards described in TG/44/11.

In another aspect, the plant of tomato variety NUN 09398 TOF, or part thereof, has at least 17, 18, or more of the following distinguishing characteristics when compared to its Reference Variety as shown in Table 4, when the numerical characteristics are determined at 5% significance level and determined by type or degree for non-numerical characteristics:

1. fewer nodes between 1st inflorescence;
2. absent or very weak anthocyanin coloration of upper third of stem;
3. shorter 3rd internode length;
4. shorter 4th internode length;
5. medium green color (RHS N137B) mature leaf color;
6. indented shape of stem end of mature fruit;
7. shorter diameter of mature fruit at widest point;
8. lighter mature fruit weight;
9. medium green fruit base color at mature-green stage;
10. red color (RHS 175B) of mature fruit color;
11. yellow epidermis color;
12. moderately compressed to medium ratio of fruit length/width;
13. very weak to weak depression at peduncle end;
14. small to medium diameter of core in cross-section in relation to total diameter;
15. long shelf life;
16. shorter mature fruit length;
17. resistant to Tobacco Mosaic Virus;
18. intermediately resistant to Tomato Brown Fruit Rugose Virus.

The disclosure also provides for a progeny of tomato variety NUN 09398 TOF. In a further aspect, the plant or progeny retains all or all but one, two, or three of the "distinguishing characteristics" or all or all but one, two, or three of the "morphological and physiological characteristics" of tomato variety NUN 09398 TOF and methods for producing that plant or progeny.

In another aspect, the disclosure provides a plant or a progeny having all the physiological and morphological characteristics of variety NUN 09398 TOF when grown under the same environmental conditions. In another aspect, the plant or progeny has all or all but one, two, or three of the physiological and morphological characteristics of tomato variety NUN 09398 TOF when measured under the same environmental conditions and e.g., evaluated at significance levels of 1%, 5%, or 10% significance (which can also be expressed as a p-value) for quantitative characteristics and determined by type or degree for non-quantitative characteristics, wherein a representative sample of seed of tomato variety NUN 09398 TOF has been deposited under Accession Number NCIMB 44028. In another aspect, the plant or progeny has all or all but one, two, or three of the physiological and morphological characteristics as listed in Tables 1-3 for variety NUN 09398 TOF when measured under the same environmental conditions and e.g., evaluated at significance levels of 1%, 5%, or 10% significance (which can also be expressed as a p-value) for quantitative characteristics and identical (same type or degree) for non-numerical characteristics.

In another aspect, the disclosure provides a seed of tomato variety NUN 09398 TOF, wherein a representative sample of said seed has been deposited under Accession Number NCIMB 44028. The disclosure also provides for a plurality of seeds of tomato variety NUN 09398 TOF. The tomato seed of variety NUN 09398 TOF may be provided as an essentially homogeneous population of tomato seed. The population of seed of tomato variety NUN 09398 TOF may be particularly defined as being essentially free from other seed. The seed population may be grown into plants to provide an essentially homogeneous population of tomato plants as described herein.

The disclosure also provides a plant grown from a seed of tomato variety NUN 09398 TOF and a plant part thereof.

The disclosure also provides a tomato fruit produced on a plant grown from a seed of tomato variety NUN 09398 TOF.

The disclosure furthermore provides a seed growing or grown on a plant of variety NUN 09398 TOF (i.e., produced after pollination of the flower of tomato variety NUN 09398 TOF).

In another aspect, the disclosure provides for a plant part obtained from tomato variety NUN 09398 TOF, wherein said plant part is: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, a cotyledon, a scion, a stock, a rootstock, a pistil, an anther, or a flower or a part thereof. Fruits are particularly important plant parts. In another aspect, the plant part obtained from tomato variety NUN 09398 TOF is a cell, optionally a cell in a cell or tissue culture. That cell may be grown into a plant of variety NUN 09398 TOF.

In another aspect, the disclosure provides a hybrid tomato variety NUN 09398 TOF.

The disclosure also provides a cell culture of tomato variety NUN 09398 TOF and a plant regenerated from tomato variety NUN 09398 TOF, wherein the plant has all or all but one, two, or three of the characteristics of tomato variety NUN 09398 TOF when grown under the same environmental conditions, as well as methods for culturing and regenerating tomato variety NUN 09398 TOF. Alternatively, a regenerated plant may have one characteristic that is different from tomato variety NUN 09398 TOF and otherwise has all the physiological and morphological characteristics of tomato variety NUN 09398 TOF when grown the same environmental conditions and wherein a representative sample of seed of said tomato variety has been deposited under Accession Number NCIMB 44028

The disclosure further provides a vegetatively propagated plant of variety NUN 09398 TOF having all or all but one, two, or three of the morphological and physiological characteristics of tomato variety NUN 09398 TOF when grown under the same environmental conditions as well as methods for vegetatively propagating tomato variety NUN 09398 TOF.

In another aspect, the disclosure provides a method of producing a tomato plant comprising crossing tomato variety NUN 09398 TOF with itself or another tomato variety and selecting a progeny tomato variety from said crossing or selfing.

The disclosure also provides a method of producing a tomato plant derived from tomato variety NUN 09398 TOF.

In a further aspect, the disclosure provides a method of producing a hybrid tomato seed comprising crossing a first parent tomato plant with a second parent tomato plant and harvesting the resultant hybrid tomato seed, wherein said first parent tomato plant or second parent tomato plant is tomato variety NUN 09398 TOF. Also provided is a hybrid tomato seed produced from crossing a first parent tomato plant with a second parent tomato plant and harvesting the resultant seed, wherein said first parent tomato plant or second parent tomato plant is tomato variety NUN 09398 TOF. Moreover, the hybrid tomato plant grown from the hybrid tomato seed is provided.

In another aspect, the disclosure provides a method of introducing a single locus conversion into the plant of variety NUN 09398 TOF, wherein a representative sample of seed of said tomato variety has been deposited under Accession Number NCIMB 44028, wherein the plant comprises the single locus conversion and otherwise has all of the morphological and physiological characteristics of tomato variety NUN 09398 TOF.

In yet another aspect, the disclosure provides a method of introducing a desired trait into tomato variety NUN 09398 TOF, said method comprises transforming the plant of variety NUN 09398 TOF with a transgene that confers the desired trait, wherein the transformed plant contains the desired trait and otherwise has all of the morphological and physiological characteristics of tomato variety NUN 09398 TOF.

The disclosure also provides a method of producing a modified tomato plant with a desired trait, wherein the method comprises mutating the tomato plant or plant part of tomato variety NUN 09398 TOF, wherein a representative sample of seed of said tomato variety has been deposited under Accession Number NCIMB 44028, and wherein the mutated plant contains the desired trait and otherwise has all of the morphological and physiological characteristic of tomato variety NUN 09398 TOF.

In another aspect, the disclosure provides a method of producing a modified tomato plant, wherein the method comprises mutating a target gene by targeted gene editing in a tomato plant or part of tomato variety NUN 09398 TOF, wherein the target gene modifies a desired trait.

In one aspect, the single locus conversion or desired trait is yield, size, shape, color, flavor or taste, storage properties, nutritional quality, post-harvest quality, male sterility, herbicide tolerance, insect resistance, pest resistance, disease resistance, environmental stress tolerance, modified carbohydrate metabolism, modified protein metabolism, or ripening.

In another aspect, the disclosure provides a container comprising the plant, plant part, or seed of tomato variety NUN 09398 TOF.

Also provided is a food, a feed, or a processed product comprising the plant part of tomato variety NUN 09398 TOF, wherein the plant part is a tomato fruit or part thereof.

DEFINITIONS

Figure 1:
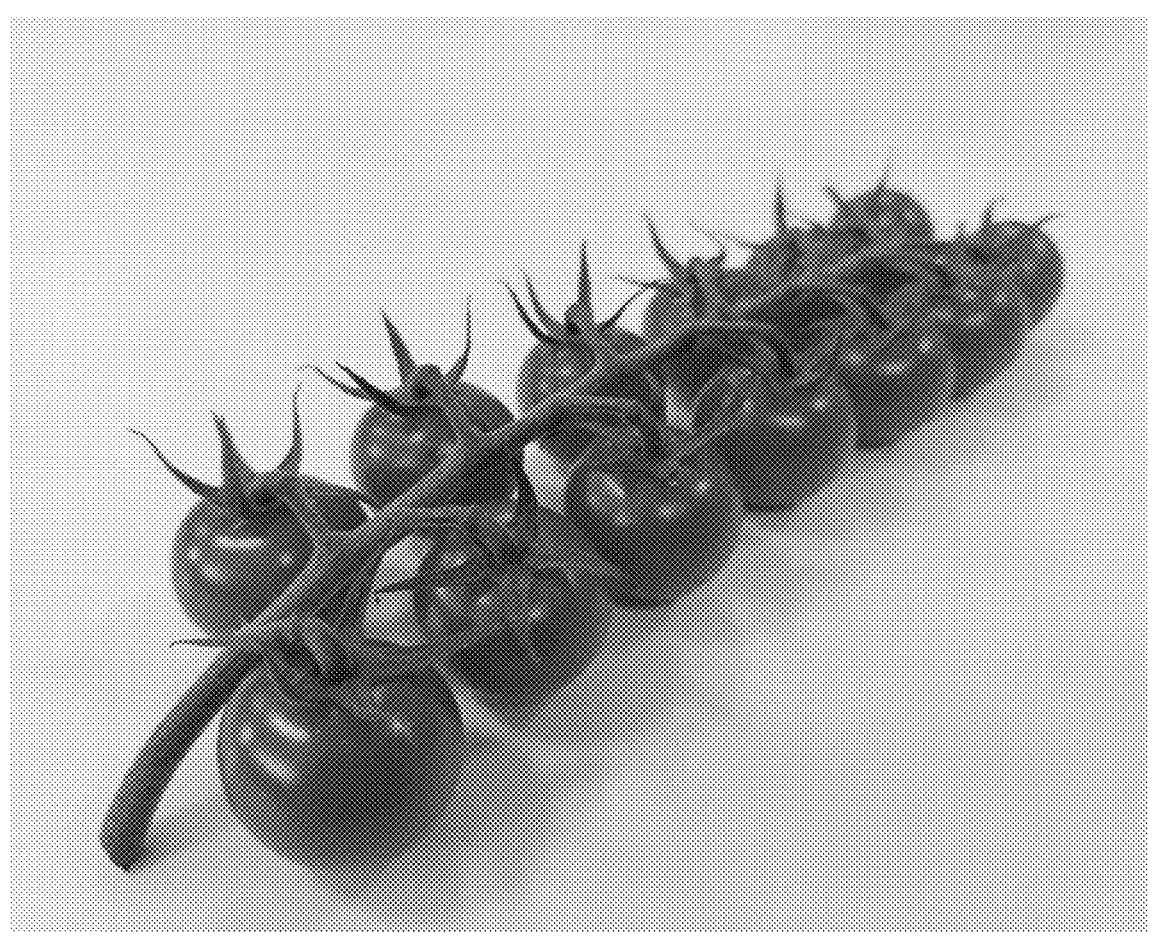
FIG. 1 shows the fruit of tomato variety NUN 09398 TOF.
Figure 2:
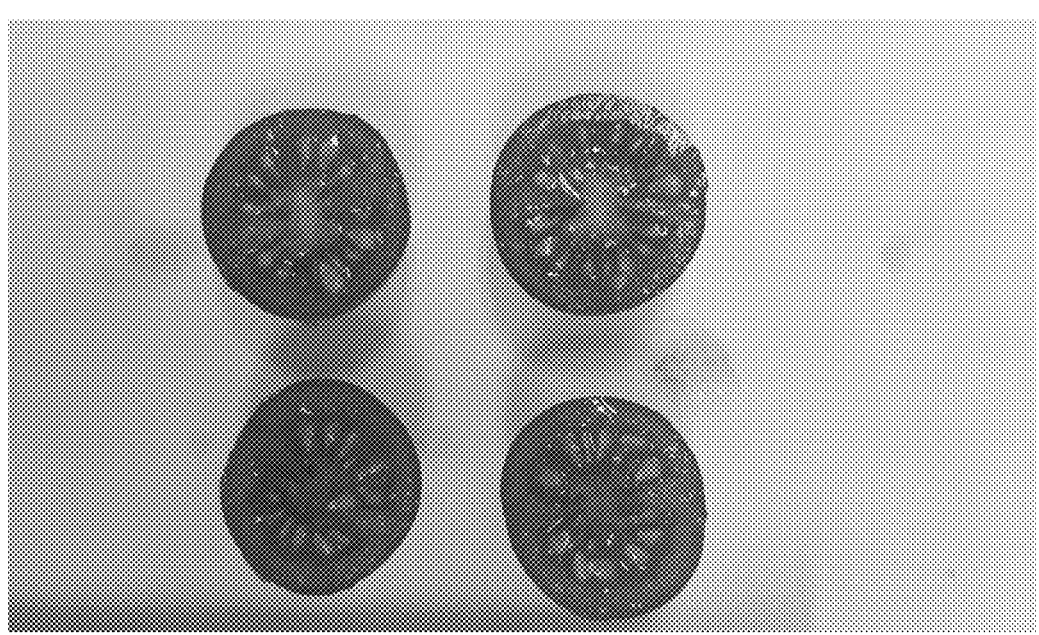
FIG. 2 shows the cross section of tomato variety NUN 09398 TOF.

"Tomato" refers herein to plants of the species *Solanum lycopersicum*, or a closely related species, and fruits thereof. *Solanum lycopersicum* is also known as *Lycopersicon lycopersicum* (L.) H. Karst. or *Lycopersicon esculentum* Mill. The most commonly eaten part of a tomato is the fruit or berry.

"Cultivated tomato" refers to plants of *Solanum lycopersicum*, or a closely related species (e.g., varieties, breeding lines or cultivars of the species *S. lycopersicum* as well as crossbreds thereof, or crossbreds with other *Solanum* species), cultivated by humans and having good agronomic characteristics.

The terms "tomato plant designated NUN 09398 TOF," "NUN 09398 TOF," "NUN 09398," "NUN 09398 F1," "09398 TOF," "tomato 09398," "Vitalion," or "Vitalion F1" are used interchangeably herein and refer to a tomato plant of variety NUN 09398 TOF, representative seed of which has been deposited under Accession Number NCIMB 44028.

"Plant" includes the whole plant or any parts or derivatives thereof, having the same genetic makeup as the plant from which it is obtained.

"Plant part" includes any part of a plant, such as a plant organ (e.g., harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, a hypocotyl, a cotyledon, a scion, a graft, a stock, a rootstock, a pistil, an anther, and a flower or a part thereof. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises one or two sets of chromosomes derived from the parent plant, e.g., from tomato variety NUN 09398 TOF. An F2 progeny produced from self-pollination of tomato variety NUN 09398 TOF will thus comprise two sets of chromosomes derived from tomato variety NUN 09398 TOF, while an F2 progeny derived from cross-fertilization of tomato variety NUN 09398 TOF will comprise only one set of chromosomes from tomato variety NUN 09398 TOF, and the other set of chromosomes from the other parent.

A "seed of tomato variety NUN 09398 TOF" refers to a tomato seed which can be grown into a plant of variety NUN 09398 TOF, wherein a representative sample of viable seed of tomato variety NUN 09398 TOF has been deposited under Accession Number NCIMB 44028. A seed can be in any stage of maturity, for example, a mature, viable seed, or an immature, non-viable seed. A seed comprises an embryo and maternal tissues.

An "embryo of tomato variety NUN 09398 TOF" refers to an "F1 hybrid embryo" as present in a seed of tomato variety NUN 09398 TOF, a representative sample of said seed of tomato variety NUN 09398 TOF has been deposited under Accession Number NCIMB 44028.

A "seed grown on tomato variety NUN 09398 TOF" refers to a seed grown on a mature plant of variety NUN 09398 TOF or inside a fruit of tomato variety NUN 09398 TOF. The "seed grown on NUN 09398 TOF" contains tissues and DNA of the maternal parent, tomato variety NUN 09398 TOF.

A "fruit of NUN 09398 TOF" refers to a fruit containing maternal tissues of tomato variety NUN 09398 TOF as has been deposited under Accession Number NCIMB 44028. The fruit comprises pericarp, septa, epidermis, columella, locular cavity, vascular bundles and optionally seed. Pericarp, septa, epidermis, columella, locular cavity, vascular bundles, and seed coat of the seed are maternal tissues, e.g., they are genetically identical to the plant on which they grow. In one aspect, the fruit contains seed grown on tomato variety NUN 09398 TOF. In another aspect, the fruit does not contain seed, i.e., the fruit is parthenocarpic. The skilled person is familiar with methods for inducing parthenocarpy. Those methods comprise chemically or genetically inducing parthenocarpy. Compounds suitable for chemic ally inducing parthenocarpy comprise auxins, gibberellins and cytokinins. Methods for genetically inducing parthenocarpy comprise the methods described in U.S. Pat. No. 9,125,353, US 2002/0010953, U.S. Pat. No. 6,060,648, EP 1057401 and EP 1428425, which are herein incorporated by reference in their entireties.

An "essentially homogeneous population of tomato seed" is a population of seeds where at least 97%, 98%, 99% or more of the total population of seed are seeds of tomato variety NUN 09398 TOF.

An "essentially homogeneous population of tomato plants" is a population of plants where at least 97%, 98%, 99% or more of the total population of plants are plants of tomato variety NUN 09398 TOF.

The phrase "essentially free from other seed" refers to a population of seed where less than 3%, 2%, 1% or less of the total population of seed is seed that is not a tomato seed or, in another aspect, less than 3%, 2%, 1% or less of the total population of seed is seed that is not seed of tomato variety NUN 09398 TOF.

"Harvest maturity" is referred to as the stage at which a tomato fruit is ripe or ready for harvest or the optimal time to harvest the fruit for the market, for processing or for consumption. In one aspect, harvest maturity is the stage which allows proper completion of the normal ripening.

"Harvested plant material" refers herein to plant parts (e.g., single fruits or clusters of fruits detached from the whole plant), which have been collected for further storage and/or further use.

"Yield" means the total weight of all tomato fruits harvested per hectare of a particular line or variety. It is understood that "yield" expressed as weight of all tomato fruits harvested per hectare can be obtained by multiplying the number of plants per hectare times the "yield per plant".

"Marketable yield" means the total weight of all marketable tomato fruits, especially fruit which is not cracked, damaged or diseased, harvested per hectare of a particular line or variety. A "marketable fruit" is a fruit that has commercial value.

"Rootstock" or "stock" refers to the plant selected for its roots, in particular for the resistance of the roots to diseases or stress (e.g., heat, cold, salinity etc.). Normally, the quality of the fruit of the plant providing the rootstock is less important.

"Scion" refers to a part of the plant attached to the rootstock. This plant is selected for its stems, leaves, flowers, or fruits. The scion contains the desired genes to be duplicated in future production by the stock/scion plant and may produce the desired tomato fruit.

"Stock/scion" or grafted plant refers to a tomato plant comprising a rootstock from one plant grafted to a scion from another plant.

"USDA descriptors" are the plant variety descriptors for tomato (*Solanum lycopersicum* or *Lycopersicon esculentum* Mill.) as published by the US Department of Agriculture, Agricultural Marketing Service, Plant Variety Protection Office, Beltsville (June 2015) and which can be downloaded from the world wide web at ams.usda.gov under services/plant-variety-protection/pvpo-c-forms under tomato. "Non-USDA descriptors" are other descriptors suitable for describing tomato.

"UPOV descriptors" are the plant variety descriptors described for tomato in the "Guidelines for the Conduct of Tests for Distinctness, Uniformity and Stability, TG/44/11 (Geneva 2011, revised 2019), as published by UPOV (International Union for the Protection of New Varieties and Plants, and which can be downloaded from the world wide web at upov.int/under edocs/tgdocs/en/tg044.pdf and is herein incorporated by reference in its entirety. Likewise, "UPOV methods" to determine specific parameters for the characterization of tomato are described at upov.int.

"Calibration Manual: DUS Test for Tomato" refers to the calibration book for tomato which provides guidance for describing a tomato variety, as published by Naktuinbow (Netherlands) and NCSS/NARO (Japan), January 2020 and based on the UPOV TG/44/11.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007.

"Reference Variety" refers herein to variety NUN 09231 TOF, a commercial variety from Nunhems B. V, also designated Adorion. The characteristics of tomato variety NUN 09398 TOF are compared with the characteristics of the Reference Variety as described in Tables 2 and 3. The distinguishing characteristics of tomato variety NUN 09398 TOF and the Reference Variety are presented on Table 4.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two, or three of the physiological and morphological characteristics" of a referred-to-plant, or "all the physiological and morphological characteristics" of Tables 1-3 or "all or all but one, two or three of the physiological and morphological characteristics" of Tables 1-3.

The physiological and/or morphological characteristics mentioned above are commonly evaluated at significance levels of 1%, 5%, or 10% if they are numerical (quantitative), or for having an identical degree (or type) if not numerical (not quantitative), if measured under the same environmental conditions. For example, a progeny plant or a Single Locus Converted plant or a mutated plant of variety NUN 09398 TOF may have one or more (or all) of the essential physiological and/or morphological characteristics of said variety listed in Tables 1-3, as determined at the 5% significance level (i.e., p<0.05) for numerical characteristics and determined by type or degree for non-numerical characteristics when grown under the same environmental conditions.

"Distinguishing characteristics" or "distinguishing morphological and/or physiological characteristics" refers herein to the characteristics which distinguish (i.e., are different) between the new variety and other tomato varieties, such as the Reference Variety when grown under the same environmental conditions. When comparing tomato variety NUN 09398 TOF with different varieties, the distinguishing characteristics may be different. The distinguishing characteristics between tomato variety NUN 09398 TOF and the Reference Variety are described in Table 4. In one aspect, the distinguishing characteristics may therefore include at least one, two, three or more (or all) of the characteristics listed in Tables 1-3. All numerical distinguishing characteristics are statistically significantly different at p<0.05 between tomato variety NUN 09398 TOF, and the other variety. All non-numerical distinguishing characteristics are different (in type or degree) between tomato variety NUN 09398 TOF and the other variety.

Tomato variety NUN 09398 TOF has the following distinguishing characteristics when compared to the Reference Variety as described in Table 4, when the numerical characteristics are determined at 5% significance level and determined by type or degree for non-numerical characteristics.

1. fewer nodes between 1st inflorescence;
2. absent or very weak anthocyanin coloration of upper third of stem;
3. shorter 3rd internode length;
4. shorter 4th internode length;
5. medium green color (RHS N137B) mature leaf color;
6. indented shape of stem end of mature fruit;
7. shorter diameter of mature fruit at widest point;
8. lighter mature fruit weight;
9. medium green fruit base color at mature-green stage;
10. red color (RHS 175B) of mature fruit color;
11. yellow epidermis color;
12. moderately compressed to medium ratio of fruit length/width;
13. very weak to weak depression at peduncle end;
14. small to medium diameter of core in cross-section in relation to total diameter;
15. long shelf life;
16. shorter mature fruit length;
17. resistant to Tobacco Mosaic Virus;
18. intermediately resistant to Tomato Brown Fruit Rugose Virus.

Thus, a tomato plant "comprising the distinguishing characteristics of tomato variety NUN 09398 TOF" (such as a progeny plant) refers herein to a plant which does not differ significantly from said variety in the distinguishing characteristics above. Therefore, in one aspect, a plant (such as a progeny plant of variety NUN 09398 TOF) is provided which does not differ significantly from tomato variety NUN 09398 TOF in the distinguishing characteristics above.

Similarity and differences between two different plant lines or varieties can be determined by comparing the number of morphological and/or physiological characteristics (e.g., the characteristics as listed in Tables 1-3) that are the same (i.e., statistically not significantly different) or that are different (i.e., statistically significantly different) between the two plant lines or varieties when grown under the same environmental conditions. A numerical characteristic is considered to be "the same" when the value for a numeric characteristic is not significantly different at the 1% (p<0.01) or 5% (p<0.05) significance level, using the T-Test, a standard method known to the skilled person. A non-numerical characteristic is considered to be "the same" when the values have the same "degree" or "type" when scored using USDA and/or UPOV descriptors for plants grown under the same environmental conditions.

In one aspect, a statistical analysis of quantitative characteristics showing the degree of significance may be provided. Statistical significance is the likelihood that a relationship between two or more variables is caused by something other than chance, i.e., that the differences in the means for quantitative characteristics of tomato variety NUN 09398 TOF and the Reference Variety are significant or due to chance. For the purpose of proving differences or distinction between tomato variety NUN 09398 TOF and the Reference Variety, a p-value of 5% (0.05) or lower is considered statistically significant. This means that there is only a 5% probability that the observed result could have happened just by chance or random variation.

The statistical analysis is drawn from a small sample of at least 15 plants or plant parts of tomato variety NUN 09398 TOF and the Reference Variety. Statistical points or parameters such as mean, minimum, median, maximum, and standard deviation are collected from the sample data to analyze where the average is, how varied the data set is, and whether the data is skewed. For the purpose of determining whether the result of a data set is statistically significant, a T-test is used, a statistical tool for proving significance of means of the two groups (e.g., tomato variety NUN 09398 TOF and the Reference Variety) at 5% significance level (p-value of 5% or 0.05).

The term "traditional breeding techniques" encompasses herein crossing, selfing, selection, doubled haploid production, embryo rescue, protoplast fusion, marker assisted selection, mutation breeding, etc. as known to the breeder (e.g., methods other than genetic modification/transformation/transgenic methods), by which, for example, a genetically heritable trait can be transferred from one tomato line or variety to another.

"Variety," "cultivated tomato," or "cultivar" means a plant grouping within a single botanical taxon of the lowest known rank.

A "plant line" is, for example, a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Progeny" as used herein refers to a plant obtained from a plant designated tomato variety NUN 09398 TOF. A progeny may be obtained by regeneration of cell culture or tissue culture or parts of a plant of said variety or selfing of a plant of said variety or by producing seeds of a plant of said variety. In a further aspect, progeny may also encompass plants obtained from crossing of at least one plant of said variety with another tomato plant of the same variety or another variety or (breeding) line, or with wild tomato plants. A progeny may comprise a mutation or a transgene. A "first generation progeny" or is the progeny directly derived from, obtained from, obtainable from or derivable from the parent plant by, e.g., traditional breeding methods (selfing and/or cross-pollinating) or regeneration (optionally combined with transformation and mutation). Thus, a plant of variety NUN 09398 TOF is the male parent, the female parent or both of a first generation progeny of that variety. Progeny may have all the physiological and morphological characteristics of variety NUN 09398 TOF when grown under the same environmental conditions. Using common breeding methods such as backcrossing or recurrent selection, mutation or transformation, one or more specific characteristics may be introduced into said variety, to provide a plant comprising all but 1, 2, or 3 or more of the morphological and physiological characteristics of tomato variety NUN 09398 TOF (e.g., as listed in Tables 1-3).

"Tissue culture" or "cell culture" refers to a composition comprising isolated cells of the same or a different type or a collection of such cells organized into parts of a plant. Tissue culture of various tissues of tomato and regeneration of plants therefrom is well known and widely published (see, e.g., Bhatia et al. (2004), Plant Cell, Tissue and Organ Culture 78: 1-21). Similarly, methods of preparing cell cultures are known in the art.

"Vegetative propagation," "vegetative reproduction," or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Regeneration" refers to the development of a plant from cell culture or tissue culture or vegetative propagation.

"Crossing" refers to the mating of two parent plants. The term encompasses "cross-pollination" and "selfing".

"Selfing" refers to self-pollination of a plant, i.e., the transfer of pollen from the anther to the stigma of the same plant.

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant." The technique can also be used on a parental line of a hybrid.

The terms "gene converted" or "conversion plant" or "single locus converted plant" in this context refer to tomato plants which are developed by traditional breeding techniques e.g., backcrossing, or via genetic engineering or through mutation breeding, wherein essentially all of the desired morphological and physiological characteristics of the parent variety or line are recovered, in addition to the one or more genes transferred into the parent via e.g., backcrossing technique (optionally including reverse breeding or reverse synthesis of breeding lines). It is understood that only the addition of a further characteristic (e.g., addition of gene conferring a further characteristic, such as a disease resistance gene), but also the replacement/modification of an existing characteristic by a different characteristic is encompassed herein (e.g., mutant allele of a gene can modify the phenotype of a characteristic).

Likewise, a "Single Locus Converted (Conversion) Plant" refers to plants developed by plant breeding techniques comprising or consisting of mutation and/or by genetic transformation and/or by traditional breeding techniques, such as backcrossing, wherein essentially all of the desired morphological and physiological characteristics of a tomato variety are recovered in addition to the characteristics of the single locus having been transferred into the variety via the backcrossing technique. In case of a hybrid, the gene may be introduced in the male or female parental line.

"Transgene" refers to a genetic locus comprising a DNA sequence which has been introduced into the genome of a tomato plant by transformation. A plant comprising a transgene stably integrated into its genome is referred to as "transgenic plant."

"Locus" (plural loci) refers to the specific location of a gene or DNA sequence on a chromosome. A locus may confer a specific trait.

"Genotype" refers to the genetic composition of a cell or organism.

"Allele" refers to one or more alternative forms of a gene locus. All of these loci relate to one trait. Sometimes, different alleles can result in different observable phenotypic traits. However, many variations at the genetic level result in little or no observable variation.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

DETAILED DESCRIPTION OF THE VARIOUS ASPECTS OF THE DISCLOSURE

The disclosure relates to the plant of variety NUN 09398 TOF, wherein a representative sample of seeds of said variety has been deposited under the Budapest Treaty, with Accession Number NCIMB 44028.

Tomato variety NUN 09398 TOF is a flavorful cherry tomato variety for the fresh market with intermediate resistance to Tomato Brown Fruit Rugose Virus (ToBRFV). The fruits are sweet with high Brix level between 7.6° to 9.2° and offer a unique balance of sweet taste, texture, and firmness of the skin.

The plant of tomato variety NUN 09398 TOF is characterized as generative and open plant with average vigor. Tomato variety NUN 09398 TOF is an early maturing variety, high yielding, and produces high quality cherry tomatoes year-round with long shelf life. This sweet cherry tomato grows on a long and flat cluster with a perfect fish bone shape and is pruning on 14 with long trusses with strong green parts. The variety is suitable for growing as traditional and lighted crops or heated greenhouse.

The disclosure also provides a tomato plant or part thereof having all of the physiological and morphological characteristics of tomato variety NUN 09398 TOF when grown under the same environmental conditions.

In another aspect, the plant of tomato variety NUN 09398 TOF or a progeny thereof comprises high resistance to *Passalora fulva* Race 0 and Groups A-E, Tomato Mosaic Virus (ToMV) Strains 0, 1, 2, and 1-2, and intermediate resistance (IR) to Tomato Brown Rugose Fruit Virus (ToBRFV), measured according to UPOV standards described in TG/44/11.

In another aspect, the plant of tomato variety NUN 09398 TOF or a progeny plant thereof, comprises all of the following morphological and/or physiological characteristics (i.e., average values of distinguishing characteristics, as indicated on the USDA Objective description of variety—tomato (unless indicated otherwise)) and shown in Tables 1-3, where the numerical characteristics are determined at the 5% significance level and the non-numerical characteristics are determined by type or degree for plants grown under the same environmental conditions. A part of this plant is also provided.

The disclosure further provides a tomato plant which does not differ from the physiological and morphological characteristics of the plant of variety NUN 09398 TOF as determined at the 1%, 2%, 3%, 4%, or 5% significance level for numerical characteristics and determined by type or degree for non-numerical characteristics when grown under the same environmental conditions. In a particular aspect, the plants are measured in the same trial (e.g., the trial is conducted as recommended by USDA or UPOV). The disclosure also comprises a part of said plant, preferably a fruit or a part thereof.

The morphological and/or physiological differences between two different individual plants described herein (e.g., between tomato variety NUN 09398 TOF and a progeny of tomato variety NUN 09398 TOF) or between a plant of variety NUN 09398 TOF or progeny of said variety, or a plant having all, or all but 1, 2, or 3, of the physiological and morphological characteristics of tomato variety NUN 09398 TOF, (or all, or all but 1, 2, or 3 of the characteristics as listed in Tables 1-3) and another known variety can easily be established by growing said variety next to each other or next to the other variety (in the same field, under the same environmental conditions), preferably in several locations which are suitable for tomato cultivation, and measuring morphological and/or physiological characteristics of a representative number of plants (e.g., to calculate an average value and to determine the variation range/uniformity within the variety). For example, trials can be carried out in Acampo California, USA (N 38 degrees 07'261"/W 121 degrees 18' 807", USA), whereby various characteristics, for example, maturity, days from seeding to harvest, plant habit, plant attitude, stem branching, leaf color, inflorescence, shape of calyx, fruit shape, number of locules, fruit pattern, fruit color, flesh color, fruit size, disease resistance, insect resistance, can be measured and directly compared for species of tomato.

Thus, the disclosure comprises tomato plant having one, two, or three physiological and/or morphological characteristics which are different from those of the plant of variety NUN 09398 TOF and which otherwise has all the physiological and morphological characteristics of the plant of variety NUN 09398 TOF, e.g., determined at the 5% significance level for numerical characteristics and determined by type or degree for non-numerical characteristics for plants grown under the same environmental conditions. In another aspect, the different characteristic is the result of a mutation (e.g., spontaneous mutation or a human induced mutation through e.g., targeted mutagenesis or traditional mutagenesis such as chemically or radiation induced mutagenesis), or it is the result of transformation.

The disclosure further relates to tomato variety NUN 09398 TOF, which when compared to its Reference Variety has the following distinguishing characteristics as shown in Table 4, when the numerical characteristics are determined at 5% significance level and determined by type or degree for non-numerical characteristics. Also encompassed are parts of the plant.

1. fewer nodes between 1st inflorescence;
2. absent or very weak anthocyanin coloration of upper third of stem;
3. shorter 3rd internode length;
4. shorter 4th internode length;
5. medium green color (RHS N137B) mature leaf color;
6. indented shape of stem end of mature fruit;
7. shorter diameter of mature fruit at widest point;
8. lighter mature fruit weight;
9. medium green fruit base color at mature-green stage;
10. red color (RHS 175B) of mature fruit color;
11. yellow epidermis color;
12. moderately compressed to medium ratio of fruit length/width;
13. very weak to weak depression at peduncle end;
14. small to medium diameter of core in cross-section in relation to total diameter;
15. long shelf life;
16. shorter mature fruit length;
17. resistant to Tobacco Mosaic Virus;
18. intermediately resistant to Tomato Brown Fruit Rugose Virus.

The disclosure also relates to a seed of tomato variety NUN 09398 TOF, wherein a representative sample of said seed has been deposited under the Budapest Treaty, with Accession Number NCIMB 44028.

In another aspect, a seed of hybrid variety NUN 09398 TOF is obtainable by crossing the male parent of said variety with the female parent of said variety and harvesting the seeds produced on the female parent. The resultant seeds of said variety can be grown to produce plants of said variety.

In another aspect, the disclosure provides a tomato plant grown from a seed of tomato variety NUN 09398 TOF and a plant part thereof.

In another aspect, the disclosure provides for a tomato plant part of variety NUN 09398 TOF, preferably a fruit or part thereof, a representative sample of seed from said variety has been deposited under the Budapest Treaty, with Accession Number NCIMB 44028

In another aspect, the different characteristic(s) is/are result of breeding with tomato variety NUN 09398 TOF and selection of progeny plant comprising 1, 2, or 3 characteristics which are different than in tomato variety NUN 09398 TOF.

Also provided is a plant of tomato variety NUN 09398 TOF, or a fruit, or other plant part thereof, produced from a seed, wherein a representative sample of said seeds has been deposited under the Budapest Treaty, with Accession Number NCIMB 44028.

Also provided is a plant part obtained from variety NUN 09398 TOF, wherein said plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, a cotyledon, a scion, a stock, a rootstock, a pistil, an anther, and a flower or a part thereof. Such plant parts may be suitable for sexual reproduction (e.g. a pollen, a flower or part thereof), vegetative reproduction (e.g., a cutting, a root, a stem, a cell, a protoplast, a leaf, a cotyledon, a hypocotyl, a cell, a root, a root tip, an anther, a flower, a seed, or a stem). Fruits are particularly important plant parts. Fruits may be parthenocarpic, or seedless, or contain immature and/or nonviable seeds.

In a further aspect, the plant part obtained from variety NUN 09398 TOF is a cell, optionally a cell in a cell or tissue culture. That cell may be grown into a plant of variety NUN 09398 TOF. A part of tomato variety NUN 09398 TOF (or of progeny of that variety or of a plant having all physiological and/or morphological characteristics but one, two, or three which are different from those of tomato variety NUN 09398 TOF) further encompasses any cells, tissues, or organs obtainable from the seedlings or plants in any stage of maturity.

The disclosure also provides a tissue or cell culture comprising cells of tomato variety NUN 09398 TOF. Such a tissue culture can, for example, be grown on plates or in liquid culture, or be frozen for long term storage. The cells of tomato variety NUN 09398 TOF used to start the culture can be selected from any plant part suitable for vegetative reproduction, or, in a particular aspect, can be one or more of an embryo, a meristem, a cotyledon, a hypocotyl, pollen, a leaf, an anther, a root, a root tip, a pistil, a petiole, a flower, a fruit, seed, or a stem of tomato variety NUN 09398 TOF. In another particular aspect, the tissue culture does not contain somaclonal variation or has reduced somaclonal variation. The skilled person is familiar with methods to reduce or prevent somaclonal variation, including regular reinitiation.

In one aspect, the disclosure provides a tomato plant regenerated from the tissue or cell culture of tomato variety NUN 09398 TOF, wherein the regenerated plant is not significantly different from tomato variety NUN 09398 TOF in all, or all but one, two, or three, of the physiological and morphological characteristics, e.g., determined at the 5% significance level for numerical characteristics and determined by type or degree for non-numerical characteristics when grown under the same environmental conditions. Optionally, the plant has one, two, or three of the physiological and morphological characteristics that are affected by a mutation or transformation with a transgene.

In another aspect, the disclosure provides a tomato plant regenerated from the tissue or cell culture of tomato variety NUN 09398 TOF, wherein the plant has all of the physiological and morphological characteristics of said variety, e.g., determined at the 5% significance level for numerical characteristics and determined by type or degree for non-numerical characteristics when grown under the same environmental conditions. Similarity or difference of a characteristic is determined by measuring the characteristics of a representative number of plants grown under the same environmental conditions, determining whether type/degree characteristics are the same or different and determining whether numerical characteristics are different at the 5% significance level.

Tomato variety NUN 09398 TOF, or its progeny, or a plant having all physiological and/or morphological characteristics but one, two, or three which are different from those of tomato variety NUN 09398 TOF, can also be reproduced using vegetative reproduction methods. Therefore, the disclosure provides for a method of producing a plant, or plant part of variety NUN 09398 TOF, comprising vegetative propagation of tomato variety NUN 09398 TOF. Vegetative propagation comprises regenerating a whole plant from a plant part of variety NUN 09398 TOF, from a progeny or from or a plant having all physiological and/or morphological characteristics of said variety but one, two, or three different characteristics, such as a cutting, a cell culture, or a tissue culture.

The disclosure also provides methods of vegetatively propagating a part of the plant of tomato variety NUN 09398 TOF. In certain aspects, the method comprises: (a) collecting tissue or cells capable of being propagated from tomato variety NUN 09398 TOF; (b) cultivating said tissue or cells to obtain proliferated shoots; and (c) rooting said proliferated shoots, to obtain rooted plantlets. Steps (b) and (c) may also be reversed, i.e., first cultivating said tissue to obtain roots and then cultivating the tissue to obtain shoots, thereby obtaining rooted plantlets. The rooted plantlets may then be further grown, to obtain plants. In one aspect, the method further comprises step (d) growing plants from said rooted plantlets. Therefore, the method also comprises regenerating a whole plant from said part of tomato variety NUN 09398 TOF. In a particular aspect, the part of the plant to be propagated is is a cutting, a cell culture, or a tissue culture.

The disclosure also provides for a vegetatively propagated plant of variety NUN 09398 TOF (or from progeny of tomato variety NUN 09398 TOF or from or a plant having all but one, two, or three physiological and/or morphological characteristics of said variety), wherein the plant has all of the morphological and physiological characteristics of tomato variety NUN 09398 TOF, e.g., determined at the 5% significance level for numerical characteristics and determined by type or degree for non-numerical characteristics for plants grown under the same environmental conditions. In another aspect, the propagated plant has all but one, two, or three of the morphological and physiological characteristics of tomato variety NUN 09398 TOF, e.g., determined at the 5% significance level for numerical characteristics and determined by type or degree for non-numerical characteristics for plants grown under the same environmental conditions. A part of said propagated plant or said propagated plant with one, two, or three differences is also provided. In another aspect, the propagated plant has all or all but one, two, or three of the morphological and physiological characteristics of tomato variety NUN 09398 TOF (e.g., as listed in Tables 1-3).

In another aspect, the disclosure provides a method for producing a tomato plant part, preferably a fruit, comprising growing the plant of variety NUN 09398 TOF until it sets at least one fruit, and collecting the fruit. Preferably, the fruit is collected at harvest maturity.

In another aspect, the fruit is collected when the seed is ripe. A plant of variety NUN 09398 TOF can be produced by seeding directly in the soil (e.g., field) or by germinating the seeds in controlled environment conditions (e.g., greenhouses, hydroponic cultures, etc.) and optionally then transplanting the seedlings into the field. For example, the seed can be sown into prepared seed beds where they will remain for the entire production the crop (see, e.g., Hartz, et. al., University of California Division of Agriculture and Natural Resources, Publication 7228, 1-5). Tomatoes can be grown with a support system such as poles (i.e., stakes) to keep the fruit from touching the ground or as bushes without support. Alternatively, plastic row covers can also be used to control the temperature. Mulches or plastic tunnels can also be used to protect the plant from frost (see, e.g., Le Strange, et. al., University of California Division of Agriculture and Natural Resources, Publication 8017, 1-8). Tomato can also be grown entirely in greenhouses or net houses. Moreover, said variety can be grown in hydroponic cultures as described herein in, e.g., US 2008/0222949, which is herein incorporated by reference in its entirety, and the skilled person is familiar with various type of hydroponic cultures.

In another aspect, the plant and plant parts of tomato variety NUN 09398 TOF and progeny of said variety, e.g., grown from seeds, produced by sexual or vegetative reproduction, regenerated from the above-described plant parts, or regenerated from cell or tissue culture of the tomato variety NUN 09398 TOF, in which the reproduced (seed propagated or vegetatively propagated) plant has all of the physiological and morphological characteristics of tomato variety NUN 09398 TOF, e.g., as listed in Tables 1-3. In one aspect, said progeny of tomato variety NUN 09398 TOF can be modified in one, two, or three characteristics, in which the modification is a result of mutagenesis or transformation with a transgene.

In another aspect, the disclosure provides a progeny plant of variety NUN 09398 TOF such as a progeny plant obtained by further breeding of tomato variety NUN 09398 TOF. Further breeding with tomato variety NUN 09398 TOF includes selfing that variety one or more times and/or cross-pollinating tomato variety NUN 09398 TOF with another tomato plant or variety one or more times. In particular, the disclosure provides for a progeny plant that retains all the essential morphological and physiological characteristics of tomato variety NUN 09398 TOF or, in another aspect, a progeny plant that retains all, or all but one, two, or three, of the morphological and physiological characteristics of tomato variety NUN 09398 TOF, optionally all or all but one, two, or three of the characteristics as listed in Tables 1-3 when grown under the same environmental conditions, determined at the 5% significance level for numerical characteristics and determined by type or degree for non-numerical characteristics. In a particular aspect, the progeny is a first generation progeny, i.e., the ovule or the pollen (or both) used in the crossing is an ovule or pollen of variety NUN 09398 TOF, where the pollen comes from an anther and the ovule comes from an ovary of tomato variety NUN 09398 TOF. In another aspect, the disclosure provides for a vegetative reproduction of the variety and a plant having all, or all but 1, 2, or 3 of the physiological and morphological characteristics of tomato variety NUN 09398 TOF (e.g., as listed in Tables 1-3).

In still another aspect, the disclosure provides a method of producing a tomato plant, comprising crossing a plant of tomato variety NUN 09398 TOF with a second tomato plant at least once, allowing seed to develop and optionally harvesting said progeny seed. The skilled person can select progeny from said crossing. Optionally, the progeny (grown from the progeny seed) is crossed twice, thrice, or four, five, six, or seven times, and allowed to set seed. In one aspect, the first "crossing" further comprises planting seeds of a first and a second parent tomato plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

The disclosure also provides a method for collecting pollen of tomato variety NUN 09398 TOF, comprising collecting pollen from a plant of variety NUN 09398 TOF. Alternatively, the method comprises growing a plant of variety NUN 09398 TOF until at least one flower contains pollen and collecting the pollen. In particular aspect, the pollen is collected when it is mature or ripe. A suitable method for collecting pollen comprises collecting anthers or the part of the anther that contains pollen, for example, by cutting the anther or the part of the anther off. Pollen can be collected in a container. Optionally, collected pollen can be used to pollinate a tomato flower.

In yet another aspect, the disclosure provides a method of producing a tomato plant, comprising selfing a plant of variety NUN 09398 TOF one or more times, and selecting a progeny plant from said selfing. In one aspect, the progeny plant retains all or all but one, two, or three of the morphological and physiological characteristics of tomato variety NUN 09398 TOF when grown under the same environmental conditions. In a different aspect, the progeny plant comprises all (or all but one, two, or three) of the physiological and morphological characteristics of tomato variety NUN 09398 TOF as listed in Tables 1-3.

The disclosure also provides a method for developing a tomato plant in a tomato breeding program, using a tomato plant described herein, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing tomato variety NUN 09398 TOF or progeny of said variety, or a plant comprising all but 1, 2, or 3 or more of the morphological and physiological characteristics of tomato variety NUN 09398 TOF (e.g., as listed in Tables 1-3), with a different tomato plant, and wherein one or more offspring of the crossing are subject to one or more plant breeding techniques: recurrent selection, backcrossing, pedigree breeding, mass selection, mutation breeding and genetic marker enhanced selection (see e.g., Vidaysky and Czosnek, (1998) Phytopathology 88(9): 910-4). For breeding methods in general, see, e.g., Principles of Plant Genetics and Breeding, (2007) George Acquaah, Blackwell Publishing, ISBN-13: 978-1-4051-3646-4.

In one aspect, pedigree selection is used as a breeding method for developing a tomato variety. Pedigree selection is also known as the "Vilmorin System of Selecton," see, e.g., Allard, John Wiley & Sons, Inc., 1999, pp. 64-67. In general, selection is first practiced among F2 plants. In the next season, the most desirable F3 lines are first identified, then desirable F3 plants within each line are selected. The following season and in all subsequent generations of inbreeding, the most desirable families are identified first, then desirable lines within the selected families are chosen. A family refers to lines that were derived from plants selected from the same progeny from the preceding generation.

Thus, progeny in connection with pedigree selection are either the generation (seeds) produced from the first cross (F1) or selfing (51), or any further generation produced by crossing and/or selfing (F2, F3, etc.) and/or backcrossing (BC1, BC2, etc.) one or more selected plants of the F1 and/or 51 and/or BC1 generation (or plants of any further generation, e.g., F2) with another tomato plant (and/or with a wild relative of tomato). Progeny may have all the physiological and morphological characteristics of tomato variety NUN 09398 TOF when grown under the same environmental conditions and/or progeny may have (be selected for having) one or more of the distinguishing characteristics of tomato variety NUN 09398 TOF.

In yet a further aspect, the disclosure provides for a method of producing a new tomato plant. The method comprises crossing tomato variety NUN 09398 TOF, or a plant comprising all but 1, 2, or 3 of the morphological and physiological characteristics of tomato variety NUN 09398 TOF (e.g., as listed in Tables 1-3), or a progeny plant thereof, either as male or as female parent, with a second tomato plant (or a wild relative of tomato) one or more times, and/or selfing a tomato plant of variety NUN 09398 TOF, or a progeny plant thereof, one or more times, and selecting progeny from said crossing and/or selfing. The second tomato plant may, for example, be a line or variety of the species *Solanum Lycopersicon, S. chilense, S. habrochaites, S. penelli, S. peruvianum, S. pimpinellifolium* or other *Solanum* species.

In a further aspect, tomato variety NUN 09398 TOF is used in crosses with other, different, tomato varieties to produce first generation (F1) tomato hybrid seeds and plants with superior characteristics. In a particular aspect, the disclosure provides a tomato seed and a plant produced by crossing a first parent tomato plant with a second parent tomato plant, wherein at least one of the first or second parent tomato plant is tomato variety NUN 09398 TOF. In another aspect, the tomato seed and plant produced are the first filial generation (F1) tomato seed and plants produced by crossing the plant of tomato variety NUN 09398 TOF with another tomato plant.

The morphological and physiological characteristics (and the distinguishing characteristics) of tomato variety NUN 09398 TOF are provided, for example, in Tables 1-3. Encompassed herein is also a plant obtainable from tomato variety NUN 09398 TOF (e.g., by selfing and/or crossing and/or backcrossing with said variety and/or progeny of said variety) comprising all or all but one, two or three of the physiological and morphological characteristics of tomato variety NUN 09398 TOF listed in Tables 1-3 as determined at the 5% significance level for numerical characteristics and determined by type or degree for non-numerical characteristics when grown under the same environmental conditions and/or comprising one or more (or all; or all except one, two or three) characteristics when grown under the same environmental conditions. The morphological and/or physiological characteristics may vary somewhat with variation in the environment (such as temperature, light intensity, day length, humidity, soil, fertilizer use), which is why a comparison under the same environmental conditions is preferred. Colors can best be measured using the Royal Horticultural Society (RHS) Chart.

In another aspect, the disclosure provides a method of producing a plant derived from a tomato variety NUN 09398 TOF, comprising crossing a plant of variety NUN 09398 TOF either as a male or female parent with a second plant or selfing tomato variety NUN 09398 TOF or vegetative reproduction of tomato variety NUN 09398 TOF and collecting seeds from said crossing or selfing or regenerating a whole plant from the vegetable cell- or tissue culture. Also provided are seeds and/or plants obtained by this method. All plants produced using tomato variety NUN 09398 TOF as a parent are within the scope of the disclosure including plant parts derived from tomato variety NUN 09398 TOF.

In further aspects, the method comprises growing a progeny plant of a subsequent generation and crossing the progeny plant of a subsequent generation with itself or a second plant and repeating the steps for additional 3-10 generations to produce a plant derived from tomato variety NUN 09398 TOF. The plant derived from tomato variety NUN 09398 TOF may be an inbred line and the aforementioned repeating crossing steps may be defined as comprising sufficient inbreeding to produce the inbred line. By selecting plants having one or more desirable traits of the line as well as potentially other selected traits.

The disclosure provides for methods of producing plants which retain all the morphological and physiological characteristics of a plant described herein. The disclosure also provides for methods of producing a plant comprising all but 1, 2, or 3 or more of the morphological and physiological characteristics of tomato variety NUN 09398 TOF (e.g., as listed in Tables 1-3), but which are still genetically closely related to said variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to variety NUN 09398 TOF if its DNA fingerprint is at least 80%, 90%, 95%, or 98% identical to the fingerprint of that variety. In a particular aspect AFLP markers are used for DNA fingerprinting (see, e.g., Vos et al. 1995, Nucleic Acid Research 23: 4407-4414). A closely related plant may have a Jaccard's Similarity index of at least about 0.8, preferably at least about 0.9, 0.95, 0.98 or more (see, e.g., Sharifova, S., et. al., (2013), Journal of Hort. Research, 21(1):83-89; Ince et al., (2010), Biochem. Genet. 48:83-95; Parvathaneni et al., (2011), J. Crop Sci. Biotech, 14 (1): 39-43; Pisanu, et. al., (2004), Acta Hort. 660, 83-89). The disclosure also provides a plant and a variety obtained or selected by applying these methods on tomato variety NUN 09398 TOF. Such a plant may be produced by crossing and/or selfing, or alternatively, a plant may simply be identified and selected amongst plants of said variety, or progeny of said variety, e.g. by identifying a variant within tomato variety NUN 09398 TOF or within progeny of said variety (e.g., produced by selfing) which variant differs from the variety described herein in one, two or three of the morphological and/or physiological characteristics (e.g., in one, two or three distinguishing characteristics), e.g., those listed in Tables 1-3. In one aspect, the disclosure provides a tomato plant having a Jaccard's Similarity index with tomato variety NUN 09398 TOF of at least 0.8, e.g. at least 0.85, 0.9, 0.95, 0.98 or even at least 0.99.

In some aspects, the disclosure provides a tomato plant comprising genomic DNA having at least 95%, 96%, 97%, 98% or 99% sequence identity compared to the genomic DNA sequence of a plant of variety NUN 09398 TOF as deposited under Accession Number NCIMB 44028. In some aspects, the tomato plant further comprises all or all but 1, 2, or 3 of the morphological and physiological characteristics of tomato variety NUN 09398 TOF (e.g., as listed in Tables 1-3). In other aspects, the tomato plant is a hybrid or other derived from a seed or plant of NUN 09398 TOF. In other aspects, the tomato plant comprises the distinguishing characteristics of tomato variety NUN 09398 TOF.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53. A full implementation of the Needleman-Wunsch global alignment algorithm is found in the needle program in The European Molecular Biology Open Software Suite (see, e.g., EMBOSS, Rice et al., Trends in Genetics June 2000, vol. 16, No. 6. pp. 276-277).

In another aspect, the plant of variety NUN 09398 TOF may also be mutated (by e.g., irradiation, chemical mutagenesis, heat treatment, etc.) and mutated seeds or plants may be selected in order to change one or more characteristics of said variety. Methods such as TILLING (Targeting Induced Local Lesions in Genomes) may be applied to tomato populations in order to identify mutants.

Similarly, tomato variety NUN 09398 TOF may be transformed and regenerated, whereby one or more chimeric genes are introduced into the variety or into a plant comprising all but 1, 2, 3, or more of the morphological and physiological characteristics (e.g., as listed in Tables 1-3). Many useful traits can be introduced into tomato variety NUN 09398 TOF by e.g., crossing a tomato variety NUN 09398 TOF with a transgenic tomato plant comprising a desired transgene, as well as by directly introducing a transgene into tomato variety NUN 09398 TOF by genetic transformation techniques.

Any pest or disease resistance genes may be introduced into a plant of variety NUN 09398 TOF, progeny of said variety or into a plant comprising all but 1, 2, or 3 or more of the morphological and physiological characteristics of tomato variety NUN 09398 TOF (e.g., as listed in Tables 1-3). Resistance to one or more of the following diseases or pests may be introduced into plants described herein: Colorado potato beetle, Southern root knot nematode, Spider mites, Sugarfly beet army worm, Tobacco flea beetle, Tomato hornworm, Tomato fruitworm, Whitefly, Bacterial canker, Bacterial soft rot, Bacterial speck, Bacterial wilt (*Pseudomonas syringae* pv. Tomato), Bacterial, Anthracnose (*Gloeosporium piperatum*), Brown rot or corky root (*Pyrenochaeta lycopersici*), *Alternaria, Fusarium* wilt (*F. oxysporum* races), Gray leaf spot (*Stemphylium* spp.), Late blight (*Phytophthora infestans* races), and Leaf mold (*Cladosporium fulvum* races), Nematode (*Meloidogyne* spp.), *Verticillium* Wilt (*Verticillium dahliae*), *Ralstonia solanacearum* (Rs), *Leveillula Taurica* (Lt), and/or *Oidium neolycopersici* (On). Other resistance genes, against pathogenic viruses (e.g., Tomato Mosaic Virus (ToMV), Curly TOF Virus, Tomato Mottle Virus, Potato Y Virus, Blotchey Ripening, Tobacco Etch Virus, the various Tobacco Mosaic Virus races, Concentric cracking, Tomato Spotted Wilt Virus (TSWV), Tomato Yellow Leaf Curl Virus (TYLCV), Gold Fleck, Tomato Torrado Virus (ToTV)), Tomato Marchitez Virus (ToMaRV), Tomato Apex Necrosis Virus (ToANV), Tomato Brown Rugose Fruit Virus (ToBRFV), fungi, bacteria, nematodes, insects or other pests may also be introduced.

Genetic transformation may, therefore, be used to insert a selected transgene into the tomato plants of the disclosure described herein or may, alternatively, be used for the preparation of transgenic tomato plants which can be used as a source of the transgene(s), which can be introduced into tomato variety NUN 09398 TOF by e.g., backcrossing. A genetic trait which has been engineered into the genome of a particular tomato plant may then be moved into the genome of another tomato plant (e.g., another variety) using traditional breeding techniques which are well-known in the art. For example, backcrossing is commonly used to move a transgene from a transformed tomato variety into an already developed tomato variety and the resulting backcross conversion plant will then comprise the transgene(s).

Any DNA sequences, whether from a different species or from the same species, which are inserted into the genome using transformation, are referred to herein collectively as "transgenes." A "transgene" also encompasses antisense, or sense and antisense sequences capable of gene silencing. Thus, the disclosure also relates to transgenic plants of tomato variety NUN 09398 TOF. In some aspects, a transgenic plant of tomato variety NUN 09398 TOF may contain at least one transgene but could also contain at least 1, 2, 3, 4, or more transgenes.

Plant transformation involves the construction of an expression vector which will function in plant cells. Such a vector comprises DNA comprising a gene under control of, or operatively linked to a regulatory element active in plant cells (e.g., promoter). The expression vector may contain one or more such operably linked gene/regulatory element combinations. The vector may be in the form of a plasmid and can be used alone or in combination with other plasmids to provided transformed tomato plants using transformation methods to incorporate transgenes into the genetic material of the tomato plant(s). Transformation can be carried out using standard methods, such as *Agrobacterium tumefaciens* mediated transformation, electroporation, biolistics particle delivery system, or microprojectile bombardment, followed by selection of the transformed cells and regeneration into plants.

Plants can also be genetically engineered, modified, or manipulated to express various phenotypes of horticultural interest. Through the transformation of tomato, the expression of genes can be altered to enhance disease resistance, insect resistance, herbicide resistance, stress tolerance, horticultural quality, and other traits. Transformation can also be used to insert DNA sequences which control or help control male sterility or fertility restoration. DNA sequences native to tomato as well as non-native DNA sequences can be transformed into tomato and used to alter levels of native or non-native proteins. Various promoters, targeting sequences, enhancing sequences, and other DNA sequences can be inserted into the genome for the purpose of altering the expression of proteins. Reduction of the specific activity of specific genes (also known as gene silencing or gene suppression) is desirable for several aspects of genetic engineering in plants.

Genome editing is another method recently developed to genetically engineer plants. Specific modification of chromosomal loci or targeted mutation can be done through sequence-specific nucleases (SSNs) by introducing a targeted DNA double strand break in the locus to be altered. Examples of SSNs that have been applied to plants are: finger nucleases (ZFNs), transcription activator-like effector nucleases (TALENs), engineered homing endonucleases or meganucleases, and clustered regularly interspaced short palindromic repeats (CRISPR)/CRISPR-associated protein 9 (Cas9), see, e.g., Songstad, et. al., Critical Reviews in Plant Sciences, 2017, 36:1, 1-23.

Thus, the disclosure also provides a method of producing a tomato plant having a desired trait comprising mutating the plant or plant part of variety NUN 09398 TOF and selecting a plant with the desired trait, wherein the mutated plant retains all or all but one, two, or three of the physiological and morphological characteristics of tomato variety NUN 09398 TOF, optionally as described in Tables 1-3, and contains the desired trait and wherein a representative sample of seed of variety NUN 09398 TOF has been deposited under Accession Number NCIMB 44028. In a further aspect, the desired trait yield, storage properties, color, flavor, size, firmness, fruit quality, enhanced nutritional quality, post-harvest quality, male sterility, herbicide tolerance, insect resistance, pest resistance, disease resistance, environmental stress tolerance, modified carbohydrate metabolism, modified protein metabolism or ripening, or wherein the desired trait comprises a mutation in any of the following genes acs2, acs4, rin, pp2c1, arf9, intense, myb12.

In one aspect, the disclosure provides a method for inducing mutation in tomato variety NUN 09398 TOF comprising:

a. exposing the seed, plant, plant part, or cell of tomato variety NUN 09398 TOF to a mutagenic compound or to radiation, wherein a representative sample of seed of said tomato variety has been deposited under Accession Number NCIMB 44028;

b. selecting the seed, plant, plant part, or cell of tomato variety NUN 09398 TOF, having a mutation; and c. optionally growing and/or multiplying the seed, plant, plant part, or cell of tomato variety NUN 09398 TOF, having the mutation.

The disclosure also provides a method of producing a tomato plant having a desired trait, wherein the method comprises transforming the tomato plant with a transgene that confers the desired trait, wherein the transformed plant contains the desired trait and otherwise retains all of the physiological and morphological characteristics of tomato variety NUN 09398 TOF. Thus, a transgenic tomato plant is provided which is produced by the method described above, wherein the plant otherwise has all of the physiological and morphological characteristics of tomato variety NUN 09398 TOF and the desired trait.

In another aspect, the disclosure provides a method of producing a progeny of plant of variety NUN 09398 TOF further comprising a desired trait, said method comprising transforming the plant of tomato variety NUN 09398 TOF with at least one transgene that confers the desired trait and/or crossing the plant of tomato variety NUN 09398 TOF with a transgenic tomato plant comprising a desired transgene so that the genetic material of the progeny that resulted from the cross contains the desired transgene(s). Also encompassed is the progeny produced by this method.

A desired trait (e.g., gene(s) conferring pest or disease resistance, or tolerance for protection, etc.) can be introduced into tomato variety NUN 09398 TOF, or progeny of said variety, by transforming said variety or progeny of said variety with a transgene that confers the desired trait, wherein the transformed plant retains all or all but one, two or three of the morphological and/or physiological characteristics of variety NUN 09398 TOF and contains the desired trait. In another aspect, the transformation or mutation confers a trait wherein the trait is yield, storage properties, color, flavor, size, firmness, fruit quality, enhanced nutritional quality, post-harvest quality, male sterility, herbicide tolerance, insect resistance, pest resistance, disease resistance, environmental stress tolerance, modified carbohydrate metabolism, modified protein metabolism or occurs in the intense gene. In a particular aspect, the specific transgene may be any known in the art or listed herein, including, a poly nucleotide sequence conferring resistance to imidazolinone, sulfonylurea, glyphosate, glufosinate, triazine, benzonitrile, cyclohexanedione, phenoxy proprionic acid and L-phosphinothricin or a polynucleotide conferring resistance to Colorado potato beetle, Southern root knot nematode, Spider mites, Sugarfly beet army worm, Tobacco flea beetle, Tomato hornworm, Tomato fruitworm, Whitefly, Bacterial canker, Bacterial soft rot, Bacterial speck, Bacterial wilt (*Pseudomonas syringae* pv. Tomato), Bacterial, Anthracnose (*Gloeosporium piperaturn*), Brown rot or corky root (*Pyrenochaeta lycopersici*), *Alternaria, Fusarium* wilt (*F. oxysporum* races), Gray leaf spot (*Stemphylium* spp.), Late blight (*Phytophthora infestans* races), and Leaf mold (*Cladosporium fulvum* races), Nematode (*Meloidogyne* spp.), *Verticillium* Wilt (*Verticillium dahliae*), *Ralstonia solanacearum* (Rs), *Leveillula Taurica* (Lt), and/ or *Oidium neolycopersici* (On). Other resistance genes, against pathogenic viruses (e.g., Tomato Mosaic Virus (ToMV), Curly TOF Virus, Tomato Mottle Virus, Potato Y Virus, Blotchey Ripening, Tobacco Etch Virus, the various Tobacco Mosaic Virus races, Concentric cracking, Tomato Spotted Wilt Virus (TSWV), Tomato Yellow Leaf Curl Virus (TYLCV), Gold Fleck, Tomato Torrado Virus (ToTV)), Tomato Marchitez Virus (ToMaRV), Tomato Apex Necrosis Virus (ToANV), Tomato Brown Rugose Fruit Virus (To-BRFV), fungi, bacteria, nematodes, insects or other pests may also be introduced.

By crossing and/or selfing (one or more), single traits may be introduced into tomato variety NUN 09398 TOF (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into tomato variety NUN 09398 TOF by breeding with said variety.

Alternatively, a single trait converted plant or single locus converted plant of variety NUN 09398 TOF may be produced by (i) genetically transforming or mutating cells of tomato variety NUN 09398 TOF; (ii) growing the cells into a plant; and (iii) optionally selecting a plant that contains the desired single locus conversion. The skilled person is familiar with various techniques for genetically transforming a single locus in a plant cell, or mutating said cells.

In another aspect, the disclosure provides a method of introducing a single locus conversion, single trait conversion, or a desired trait into tomato variety NUN 09398 TOF, comprising introducing a single locus conversion, single trait conversion, or a desired trait in at least one of the parents of tomato variety NUN 09398 TOF; and crossing the converted parent with the other parent of tomato variety NUN 09398 TOF to obtain seed of tomato variety NUN 09398 TOF.

In another aspect, the step of introducing a single locus conversion, single trait conversion, or desired trait in at least one of the parents comprises:

a. crossing the parental line of tomato variety NUN 09398 TOF with a second tomato plant comprising the single locus conversion, the single trait conversion or the desired trait;

b. selecting F1 progeny plants that contain the single locus conversion, the single trait conversion or the desired trait;

c. crossing said selected progeny plants of step b) with the parental line of step a), to produce a backcross progeny plant;

d. selecting backcross progeny plants comprising the single locus conversion, the single trait conversion or the desired trait and otherwise all or all but one, two or three of the morphological and physiological characteristics the parental line of step a) to produce selected backcross progeny plants; and e. optionally repeating steps c) and d) one or more times in succession to produce selected second, third or fourth or higher backcross progeny plants comprising the single locus conversion, the single trait conversion or the desired trait and otherwise all or all but one, two or three of the morphological and physiological characteristics the parental line of step a) to produce selected backcross progeny plants, when grown in the same environmental conditions.

The disclosure further relates to plants obtained by this method.

In another aspect, the step of introducing a single locus conversion, single trait conversion, or a desired trait in at least one of the parents comprises:

a. obtaining a cell or tissue culture of cells of the parental line of tomato variety NUN 09398 TOF;

b. genetically transforming or mutating said cells;

c. growing the cells into a plant; and d. optionally selecting plants that contain the single locus conversion, the single trait conversion or the desired trait.

In another aspect, the disclosure provides a method of introducing a single locus conversion or single trait conversion or a desired trait into tomato variety NUN 09398 TOF comprising:

a. obtaining a combination of a parental lines of tomato variety NUN 09398 TOF, optionally through reverse synthesis of breeding lines;

b. introducing a single locus conversion in at least one of the parents of step a; and c. crossing the converted parent with the other parent of step a to obtain seed of tomato variety NUN 09398 TOF.

In another method, the step of introducing a single locus conversion, single trait conversion, or a desired trait in at least one of the parents comprises genetically transforming or mutating cells of the parental line of tomato variety NUN 09398 TOF; growing the cells into a plant; and optionally selecting plants that contain the single locus conversion, the single trait conversion or the desired trait.

In any of the above methods, where the single locus conversion concerns, single trait conversion, or a desired trait, the trait may be yield or pest resistance or disease resistance. In one aspect, the trait is disease resistance and the resistance are conferred to Colorado potato beetle, Southern root knot nematode, Spider mites, Sugarfly beet army worm, Tobacco flea beetle, Tomato hornworm, Tomato fruitworm, Whitefly, Bacterial canker, Bacterial soft rot, Bacterial speck, Bacterial wilt (*Pseudomonas syringae* pv. Tomato), Bacterial, Anthracnose (*Gloeosporium piperatum*), Brown rot or corky root (*Pyrenochaeta lycopersici*), *Alternaria, Fusarium* wilt (*F. oxysporum* races), Gray leaf spot (*Stemphylium* spp.), Late blight (*Phytophthora infestans* races), and Leaf mold (*Cladosporium fulvum* races), Nematode (*Meloidogyne* spp.), *Verticillium* Wilt (*Verticillium dahliae*), *Ralstonia solanacearum* (Rs), *Leveillula Taurica* (Lt), and/or *Oidium neolycopersici* (On). Other resistance genes, against pathogenic viruses (e.g., Tomato Mosaic Virus (ToMV), Curly TOF Virus, Tomato Mottle Virus, Potato Y Virus, Blotchey Ripening, Tobacco Etch Virus, the various Tobacco Mosaic Virus races, Concentric cracking, Tomato Spotted Wilt Virus (TSWV), Tomato Yellow Leaf Curl Virus (TYLCV), Gold Fleck, Tomato Torrado Virus (ToTV)), Tomato Marchitez Virus (ToMaRV), Tomato Apex Necrosis Virus (ToANV), Tomato Brown Rugose Fruit Virus (ToBRFV), fungi, bacteria, nematodes, insects or other pests may also be introduced.

The disclosure also provides a plant having one, two, or three physiological and/or morphological characteristics which are different from those of tomato variety NUN 09398 TOF and which otherwise has all the physiological and morphological characteristics of said variety, wherein a representative sample of seed of said tomato variety has been deposited under Accession Number NCIMB 44028. In particular, variants which differ from tomato variety NUN 09398 TOF, in none, one, two, or three of the characteristics mentioned in Tables 1-3 are encompassed.

The disclosure also provides a tomato plant comprising at least a first set of the chromosomes of tomato variety NUN 09398 TOF, a sample of seed of said tomato variety has been deposited under Accession Number NCIMB 44028; optionally further comprising a single locus conversion or a mutation, wherein said plant has essentially all of the morphological and physiological characteristics of the plant comprising at least a first set of the chromosomes of said variety. In another aspect, this single locus conversion confers a trait, wherein the trait is yield, storage properties, color, flavor, size, firmness, fruit quality, enhanced nutritional quality, post-harvest quality, male sterility, herbicide tolerance, insect resistance, pest resistance, disease resistance, environmental stress tolerance, modified carbohydrate metabolism, modified protein metabolism or ripening, or wherein the desired trait comprises a mutation in any of the following genes acs2, acs4, rin, pp2c1, arf9, intense, myb12.

In another aspect, the disclosure provides for a haploid plant and/or a doubled haploid plant of tomato variety NUN 09398 TOF, or of a plant having all but one, two, or three physiological and/or morphological characteristics of tomato variety NUN 09398 TOF, or progeny of any of these. Haploid and doubled haploid (DH) plants can, for example, be produced by cell or tissue culture and chromosome doubling agents and regeneration into a whole plant. For example, DH production chromosome doubling may be induced using known methods, such as colchicine treatment or the like. In one aspect, the method comprises inducing a cell or tissue culture with a chromosome doubling agent and regenerating the cells or tissues into a whole plant.

In a further aspect, the disclosure comprises a method for making doubled haploid cells of tomato variety NUN 09398 TOF, comprising making doubled haploid cells from haploid cells from the plant or plant part of tomato variety NUN 09398 TOF with a chromosome doubling agent, such as colchicine treatment (see, e.g., Nikolova V, Niemirowicz-Szczytt K (1996) Acta Soc Bot Pol 65:311-317).

The disclosure also provides for haploid plants and/or doubled haploid plants derived from tomato variety NUN 09398 TOF that, when combined, make a set of parents of tomato variety NUN 09398 TOF. The haploid plant and/or the doubled haploid plant of tomato variety NUN 09398 TOF can be used in a method for generating parental lines of tomato variety NUN 09398 TOF.

The description also provides methods for determining the identity of parental lines of plants described herein, in particular, the identity of the female line. US 2015/0126380, which is hereby incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of a plant of variety NUN 09398 TOF or is a progeny of said variety, because the seed coat of the seed is a maternal tissue genetically identical to said variety. In one aspect, the present disclosure relates to a seed coat comprising maternal tissue of tomato variety NUN 09398 TOF. In another aspect, the disclosure relates to a tomato seed comprising a maternal tissue of tomato variety NUN 09398 TOF. In another particular aspect, the disclosure provides for a method of identifying the female parental line of tomato variety NUN 09398 TOF by analyzing the seed coat of a seed of that variety. In another aspect, the disclosure provides for a method of determining whether a seed is grown on tomato variety NUN 09398 TOF by analyzing the seed coat or another maternal tissue of said seed.

In another aspect, a combination of a male and a female parental line of tomato variety NUN 09398 TOF can be generated by methods described herein, for example, through reverse synthesis of breeding lines.

Using methods known in the art such as "reverse synthesis of breeding lines" or "reverse breeding", it is possible to produce parental lines for a hybrid plant such as tomato variety NUN 09398 TOF. A skilled person can take any individual heterozygous plant (called a "phenotypically superior plant" in Example 2 of US 2015/0245570 hereby incorporated by reference in its entirety; NUN 09398 TOF is such plant) and generate a combination of parental lines (reverse breeding parental lines) that, when crossed, produce the variety NUN 09398 TOF. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US2015/0245570 or from Wijnker et al., Nature Protocols Volume: 9, Pages: 761-772 (2014) DOI: doi: 10.1038/nprot.2014.049. Thus, the disclosure provides a method for producing parental lines for a hybrid organism (e.g., tomato variety NUN 09398 TOF), comprising in one aspect: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

In another aspect, the method for producing parental lines for hybrid organisms, e.g., of tomato variety NUN 09398 TOF, which when crossed reconstitute the genome of tomato variety NUN 09398 TOF, comprising:

a. defining a set genetic markers that are present a heterozygous form (H) in a partially heterozygous starting organism;

b. producing at least one further generation from the starting organism by self-pollination (e.g., F2 or F3 generation);

c. selecting at least one pair of progeny organisms in which at least one genetic marker from the set is present in a complementary homozygous forms (B vs. A, or A vs. B); and d. optionally repeating steps b) and c) until at least one pair of progeny organisms that have complementary alleles for at least a subset of the genetic markers has been selected as parental lines for a hybrid.

Thus, in one aspect, the disclosure relates to a method of producing a combination of parental lines of a plant of tomato variety NUN 09398 TOF comprising making doubled haploid cells from haploid cells from said plant or a seed of that plant; and optionally crossing these parental lines to produce and collecting seeds. In another aspect, the disclosure relates to a combination of parental lines produced by this method. In still another aspect, the combination of parental lines can be used to produce a seed or plant of variety NUN 09398 TOF when these parental lines are crossed. In still another aspect, the disclosure relates to a combination of parental lines from which a seed or a plant has all of the physiological and/or morphological characteristics of tomato variety NUN 09398 TOF, e.g., when the numerical characteristics are determined at the 5% significance level and determined by type or degree for non-numerical characteristics for plants grown under the same environmental conditions.

The disclosure also provides a method for producing parental lines for hybrid NUN 09398 TOF comprising: genetically characterizing a doubled haploid line from tomato variety NUN 09398 TOF to determine whether one or more genetic markers are present in a first homozygous form or in a second homozygous form in said line, wherein the one or more genetic markers are present in a heterozygous form in tomato variety NUN 09398 TOF; and selecting at least one pair of doubled haploid lines that have complementary alleles for the one or more the genetic markers, wherein each member of the pair is suitable as a parental line for a hybrid organism, optionally this method further comprises defining a set of genetic markers present in a heterozygous form in tomato variety NUN 09398 TOF; and producing doubled haploid lines from tomato variety NUN 09398 TOF. Doubled haploid lines generated as described herein can be used in such a method.

The disclosure also provides a combination of parental lines which, when crossed, produce a seed or plant having all physiological and/or morphological characteristics of tomato variety NUN 09398 TOF but one, two, or three which are different (when grown under the same environmental conditions), as well as a seed or plant having all physiological and/or morphological characteristics of tomato variety NUN 09398 TOF, but one, two, or three which are different, e.g., when the numerical characteristics are determined at the 5% significance level and determined by type or degree for non-numerical characteristics for plants grown under the same conditions.

A part of tomato variety NUN 09398 TOF (or of progeny of said variety or of a plant having all physiological and/or morphological characteristics but one, two, or three which are different from those of said variety) encompasses any cells, tissues, organs obtainable from the seedlings or plants, such as but not limited to: a tomato fruit or a part thereof, a cutting, hypocotyl, cotyledon, seed coat, pollen and the like. Such parts can be stored and/or processed further. The disclosure further provides for food or feed products comprising a part of tomato variety NUN 09398 TOF or a part of progeny of said varieties, or a part of a plant having all but one, two or three physiological and/or morphological characteristics of tomato variety NUN 09398 TOF, comprising one or more of such parts, optionally processed (such as canned, chopped, cooked, roasted, in a sauce, in a sandwich, pasted, puréed or concentrated, juiced, frozen, dried, pickled, or powdered).

In another aspect, the disclosure provides a method of determining the genotype of a plant described herein comprising detecting in the genome (e.g., a sample of nucleic acids) of the plant at least a first polymorphism or an allele. The skilled person is familiar with many suitable methods of genotyping, detecting a polymorphism or detecting an allele including SNP (Single Nucleotide Polymorphism) genotyping, restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example, by obtaining a sample of nucleic acid from a plant and detecting in said nucleic acids a plurality of polymorphisms. The method may further comprise storing the results of the step of detecting the plurality of polymorphisms on a computer readable medium.

Also provided is a plant part obtainable from variety NUN 09398 TOF or from progeny of said variety or from a plant having all but one, two, or three physiological and/or morphological characteristics which are different from those of tomato variety NUN 09398 TOF, or from a vegetatively propagated plant of variety NUN 09398 TOF (or from its progeny or from a plant having all or all but one, two, or three physiological and/or morphological characteristics which are different from those of tomato variety NUN 09398 TOF), wherein the plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed-coat or another maternal tissue which is part of a seed grown on tomato variety NUN 09398 TOF, or a hypocotyl, a cotyledon, a scion, a stock, a rootstock, a pistil, an anther, or a flower or a part thereof.

A part of the plant of variety NUN 09398 TOF (or of progeny of said variety or of a plant having all physiological and morphological characteristics but one, two, or three which are different from those of said variety) encompassed any cells, tissues, organs obtainable from the seedlings or plants, such as but not limited to a tomato fruit or part thereof, a cutting, a hypocotyl, a cotyledon, seed coat, or a pollen.

Such a plant part of tomato variety NUN 09398 TOF can be stored and/or processed further. The disclosure thus also provides for a food or a feed product comprising one or more of such parts from tomato variety NUN 09398 TOF or from progeny of said variety, or from a derived variety, such as a plant having all or all but one, two, or three of the physiological and morphological characteristics of tomato variety NUN 09398 TOF. Preferably, the plant part is a tomato fruit or part thereof and/or an extract from the fruit of tomato variety NUN 09398 TOF comprising at least a cell of tomato variety NUN 09398 TOF. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

In another aspect, the disclosure provides for a tomato fruit of variety NUN 09398 TOF, or a part of a fruit of said variety. The fruit can be in any stage of maturity, for example, immature or mature. In another aspect, the disclosure provides for a container comprising or consisting of a plurality of harvested tomato fruits or parts of fruits of said variety, or fruits of progeny thereof, or fruits of a derived variety.

Marketable tomato fruits are generally sorted by size and quality after harvest. Alternatively, the tomato fruits can be sorted by expected shelf life, pH or Brix.

In another aspect, the plant, plant part or seed of tomato variety NUN 09398 TOF is inside a container, for example, containers such as cans, boxes, crates, bags, cartons, Modified Atmosphere Packaging, films (e.g., biodegradable films), etc. comprising a plant or a part of a plant (fresh and/or processed) or a seed of tomato variety NUN 09398 TOF. In a particular aspect, the container comprises a plurality of seeds of tomato variety NUN 09398 TOF, or a plurality of plant parts of tomato variety NUN 09398 TOF. The seed may be disinfected, primed and/or treated with various compounds, such as seed coatings or crop protection compounds. The seed produces a plant of variety NUN 09398 TOF.

Tomato variety NUN 09398 TOF may also be grown for use as rootstocks (stocks) or scions. Typically, different types of tomatoes are grafted to enhance disease resistance, which is usually conferred by the rootstock, while retaining the horticultural qualities usually conferred by the scion. It is not uncommon for grafting to occur between cultivated tomato varieties and related tomato species. Methods of grafting and vegetative propagation are well-known in the art.

In another aspect, the disclosure provides to a plant comprising a rootstock or scion of tomato variety NUN 09398 TOF.

All documents (e.g., patent publications) are herein incorporated by reference in their entirety, including the following cited references:

Fruit Logistica 2022, Berlin, Germany, 5-7 Apr. 2022.

Naktuinbow (Netherlands) and NCSS/NARO (Japan), "Calibration Manual: DUS Test for Tomato," January 2020.

Tiersma, T., "We're fast-tracking this tomato variety," Fresh Plaza, published 3 Jun. 2022.

UPOV, "Guidelines for the Conduct of Tests for Distinctness, Uniformity and Stability", TG/44/11 (Geneva 2011, revised 2019), world-wide web at upov.int under edocs/tgdocs/en/tg044.pdf.

US Department of Agriculture, Agricultural Marketing Service, "Objective Description of Variety Tomato (*Solanum lycopersicum* or *Lycopersicon esculentum* Mill)", world wide web at ams.usda.gov/services/plant-variety-protection/pvpo-c-forms, under tomato.

Bhatia, P., et al., "Tissue Culture Studies of Tomato (*Lycopersicum esculentum*)", Plant Cell, Tissue and Organ Culture, 2004, vol. 78, pp. 1-21.

Hartz, T., et. al., "Processing Tomato Production in California," University of California Division of Agriculture and Natural Resources, 1996, Publication 7228, pp. 1-5.

Ince, A. G., et al., "Genetic Relationship Within and Between *Capsicum* Species", Biochem Genet, 2010, vol. 48, pp. 83-95.

Le Strange, M., et. al., "Fresh-market Production in California," University of California Division of Agriculture and Natural Resources, 2000, Publication 8017, pp. 1-8.

Needleman, S. B., et. al., "A General Method Applicable to the Search for Similarities in the Amino Acid Sequence of Two Proteins", Journal of Molecular Biology, 1970, vol. 48(3), pp. 443-53.

Nikolova, V., et. al., "Diploidization of Cucumber (*Cucumis sativus* L.) Haploids by Colchini Treatment", Acta Societas Botanicorum Poloniae, 1996, vol. 65, pp. 311-317.

Pisanu, A. B., et. al., "Yield and Biometric Characteristics of 9 Clones Selected from the Population of "*Spinoso sardo*" Artichokes, Acta Hort., 2004, ISHS 660, pp. 83-89.

Rice, P., et al., "EMBOSS: The European Molecular Biology Open Software Suite", Trends in Genetics, 2000, vol. 16, Issue 6. pp. 276-277.

Sharifova, S., et. al., "Assessment of Genetic Diversity in Cultivated Tomato (*Solanum lycopersicum* L.) Genotypes Using RAPD Primers", Journal of Horticultural Research, 2013, vol. 21, no. 1, pp. 83-89.

Vidaysky, F., et. al., "Tomato Breeding Lines Resistant and Tolerant to Tomato Yellow Leaf Curl Virus Issued from *Lycopersicum hirsutum*", The American Phytopathology Society, 1998, vol. 88, no. 9, pp. 910-914.

Vos, P., et al., AFLP: A New Technique for DNA Fingerprinting 1995, Nucleic Acids Research, 1995, vol. 23, No. 21, pp. 4407-4414.

Wijnker, E., et al., Hybrid Recreation by Reverse breeding in *Arabidopsis thaliana*, Nature Protocols, 2014, vol. 9, pp. 761-772. DOI: doi: 10.1038/nprot.2014.049

U.S. Pat. No. 9,125,353

US 2002/0010953

U.S. Pat. No. 6,060,648

EP 1057401

EP 1428425

US 2008/0222949

US 2015/0126380

US 2015/0245570

Development of Tomato Variety NUN 09398 TOF

The hybrid NUN 09398 TOF was developed from a male and female proprietary inbred line of Nunhems based on yield and adaptability. The female and male parents were crossed to produce hybrid (F1) seeds of tomato variety NUN 09398 TOF. The seeds of tomato variety NUN 09398 TOF can be grown to produce hybrid plants and parts thereof (e.g., tomato fruit). The hybrid NUN 09398 TOF can be propagated by seeds or vegetatively.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that tomato variety NUN 09398 TOF is uniform and stable.

Deposit Information

A total of 625 seeds of the hybrid variety NUN 09398 TOF was made and accepted according to the Budapest Treaty by Nunhems B.V. on Jul. 9, 2022 at the NCIMB Ltd., Ferguson Building, Craibstone Estate, Bucksburn, Aberdeen AB21 9YA, United Kingdom (NCIMB). The deposit was assigned Accession Number NCIMB 44028. A statement indicating the viability of the sample has been provided. A deposit of tomato variety NUN 09398 TOF and of the male and female parent line is also maintained at Nunhems B.V. The seed lot for tomato variety NUN 09398 TOF is 32349601004.

The deposit will be maintained in NCIMB for a period of 30 years, or 5 years after the most recent request, or for the enforceable life of the patent whichever is longer and will be replaced if it ever becomes nonviable during that period. Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. Applicant does not waive any rights granted under this patent on this application or under the Plant Variety Protection Act (7 U.S.C. § 2321 et seq.). Accordingly, the requirements of 37 CFR § 1.801-1.809 have been satisfied.

Characteristics of Tomato Variety NUN 09398 TOF

The most similar variety to tomato variety NUN 09398 TOF refers herein to variety NUN 09231 TOF, a commercial variety from Nunhems B.V, also designated as Adorion.

In Table 1, the characteristics of tomato variety NUN 09398 TOF is shown based on several trials in the Netherlands in 2020. For numerical characteristics averages, were calculated. For non-numerical characteristics, the type/degree were determined.

In Tables 2 and 3, a comparison between tomato variety NUN 09398 TOF and the Reference Variety is shown based on a trial in Acampo, California, USA conducted under greenhouse conditions. Seeding date: Sep. 16, 2022; Transplating date: Oct. 20, 2022; Harvest date: Jan. 27, 2023. In Table 4, the distinguishing characteristics between tomato variety NUN 09398 OF and the Reference Variety are presented.

One replication of 30 plants of each variety, from which at least 15 plants or plants were randomly selected and used to measure characteristics. For numerical characteristics averages, were calculated. For non-numerical characteristics, the type/degree were determined. Similarity and differences between two different plant lines or varieties can be determined by comparing the number of morphological and/or physiological characteristics (e.g., the characteristics as listed in Tables 1-3) that are the same (i.e., statistically not significantly different) or that are different (i.e., statistically significantly different) between the two plant lines or varieties when grown under the same environmental conditions. A numerical characteristic is considered to be "the same" when the value for a numeric characteristic is not significantly different at the 1% ($p<0.01$) or 5% ($p<0.05$) significance level, using T-test, a standard method known to the skilled person. A non-numerical or "degree" or "type" characteristic is considered "the same" when the values have the same "degree" or "type" when scored using USDA and/or UPOV descriptors, if the plants are grown under the same environmental conditions. In one aspect, a statistical analysis using T-test at 5% significance level is provided (see, Tables 5-15).

In another aspect, the disclosure provides a tomato plant having the physiological and morphological characteristics of tomato variety NUN 09398 TOF as presented in Tables 1-3 when grown under the same environmental conditions, wherein a representative sample of said tomato variety is deposited under Accession Number NCIMB 44028.

TABLE 1

| Characteristics of Tomato Variety NUN 09398 TOF (UPOV Descriptors) | |
|---|---|
| Characteristics | Application Variety (NUN 09398 TOF) |
| Seedling: | |
| Anthocyanin coloration of hypocotyl: Absent, Present | Present |
| Plant: | |
| Growth type: Determinate, Indeterminate, Semi-determinant, Semi indeterminant | Indeterminate |
| Number of inflorescences on main stem: few, medium, many | Many |
| Height: Very short, Short, Medium, Long, Very long | Medium to long |
| Vigor: Weak, Medium, Strong | Medium |
| Stem: | |
| Anthocyanin coloration: Absent or very weak, weak, medium, strong, very strong | Absent or very weak |

TABLE 1-continued

| Characteristics of Tomato Variety NUN 09398 TOF (UPOV Descriptors) | |
| --- | --- |
| Characteristics | Application Variety (NUN 09398 TOF) |
| Length of internode: <br> Short, Medium, Long | Short |
| Stem type: <br> Stiff, flexible | Stiff |
| Leaf: | |
| Attitude in relation to main stem (in middle third of plant): <br> Semi-erect; Horizontal; Drooping | Horizontal to semi-drooping |
| Leaf density: <br> Weak, Medium, Strong | Medium |
| Length: <br> Short, Medium, Long | Medium |
| Width: <br> Narrow, Medium, Broad | Medium |
| Type of blade: <br> Pinnate, Bipinnate | Bipinnate |
| Leaf color: <br> Light green, Medium green, Dark green | Medium green |
| Size of leaflets (in middle of leaf): <br> Very small, Small, Medium, Large, Very large | Medium to large |
| Intensity of green color: <br> Very light, Light, Medium, Dark, Very dark | Medium to dark |
| Glossiness: <br> Weak, Medium, Strong | Weak to medium |
| Blistering: <br> Weak, Medium, Strong | Medium |
| Attitude of petiole of leaflet in relation to main axis: <br> Semi-erect, Horizontal, Semi-drooping | Semi-erect to horizontal |
| Flower: | |
| Inflorescence type: <br> Manly uniparous, Equally uniparous and multiparous, Mainly multiparous | Mainly uniparous |
| Fasciation (1st flower of inflorescence): | Absent |
| Color: <br> Yellow, Orange | Yellow |
| Pubescence of style: <br> Absent or very scarce, Present | Present |
| Peduncle: | |
| Abscission layer: <br> Absent, Present | Present |
| Pedicel length: <br> Short, Medium, Long | Short |
| Fruit: | |
| Green shoulder (before maturity): <br> Absent, Present | Present |
| Extent of green shoulder (before maturity): <br> Very small, Small, Medium, Large | Medium |
| Intensity of green color of shoulder (before maturity): <br> Light, Medium, Dark | Medium |
| Intensity of green color excluding shoulder (before maturity): <br> Very light, Light, Medium, Dark, Very dark | Very light to light |
| Green stripes (before maturity): <br> Absent, Present | Absent |
| Size: <br> Very small, Very small to small, Small to medium, Medium, Medium to large, Large, Large to very large, Very large | Very small |
| Uniformity of caliber: <br> Heterogeneous, Homogeneous | Homogeneous |
| Shape in longitudinal section: <br> Flattened, Oblate, Circular, Oblong, Cylindrical, Elliptic, Cordate, Ovate, Obovate, Pyriform, Obcordate | Circular |
| Ribbing at peduncle end: <br> Absent or very weak, Weak, Medium, Strong, Very strong | Absent or very weak |

TABLE 1-continued

| Characteristics of Tomato Variety NUN 09398 TOF (UPOV Descriptors) | |
| --- | --- |
| Characteristics | Application Variety (NUN 09398 TOF) |
| Depression at peduncle end: <br> Absent or very weak, Weak, Medium, Strong, Very strong | Absent or very weak |
| Cross section: <br> Round, Flattened, Angular, Irregular | Round |
| Size of peduncle scar: <br> Very small, Small, Medium, Large, Very large | Very small |
| Size of blossom scar: <br> Very small, Small, Medium, Large, Very large | Very small |
| Shape at blossom end: <br> Indented, Indented, Flat, Flat to pointed, Conical | Flat |
| Size of core in cross section: <br> Very small, Small, Medium, Large, Very thick | Small to medium |
| Thickness of pericarp: <br> Very thin, Thin, Medium, Thick, Very thick | Thin |
| Fruit neck: <br> Absent, Slightly present, Present | Absent |
| Number of locules: <br> Only two, Two or three, Three or four, Four, five, or six; More than six | Only two |
| Gel in locules: <br> Absent, Present | Present |
| Fruit base color of the fruit (before maturity): <br> Light green, Medium green, Dark green | Medium green |
| Color at maturity: <br> Cream, Yellow, Orange, Pink, Red, Brown, Green | Red |
| Color of flesh (at maturity): <br> Cream, Yellow, Orange, Pink, Red, Brown, Green | Red |
| Glossiness of skin: <br> Weak, Medium, Strong | Medium |
| Color of epidermis: <br> Colorless, Yellow | Yellow |
| Firmness: <br> Very soft, Soft, Medium, Firm, Very firm | Firm |
| Shelf life: <br> Very short, short, medium, long, very long | Long |
| Sensitivity to silvering: <br> Insensitive (tolerant to silvering), Sensitive (susceptible to silvering), Not tested | Insensitive |
| Brix level: | 7.6° to 9.2° |
| Maturity: | |
| Time of flowering (50% of the plants with at least one open flower from seed sowing): 3 = Early; 5 = Medium; 7 = Late | Early |
| Time of maturity: <br> Very early, Early, Medium, Late, Very late | Very early to early |
| Resistances: | |
| *Passalora fulva* Race 0 | Highly resistant |
| *Passalora fulva* Group A | Highly resistant |
| *Passalora fulva* Group B | Highly resistant |
| *Passalora fulva* Group C | Highly resistant |
| *Passalora fulva* Group D | Highly resistant |
| *Passalora fulva* Group E | Highly resistant |
| Tomato Mosaic Virus (ToMV) Strain 0 | Highly resistant |
| Tomato Mosaic Virus (ToMV) Strain 1 | Highly resistant |
| Tomato Mosaic Virus (ToMV) Strain 2 | Highly resistant |
| Tomato Mosaic Virus (ToMV) Strain 1-2 | Highly resistant |
| Tobacco Mosaic Virus | Present |
| Tomato Brown Rugose Fruit Virus (ToBRFV) | Intermediately resistant |

TABLE 2

| Characteristics | Application Variety (NUN 09398 TOF) | Reference Variety (NUN 09231 TOF) |
|---|---|---|
| Characteristics of Tomato Variety NUN 09398 TOF and the Reference Variety (USDA Descriptors) | | |
| Seedling: | | |
| Anthocyanin in hypocotyl of 1-15 cm seedling: absent, present | Present | Present |
| Mature plant (at maximum vegetative development): | | |
| Mature plant height, cm: | | |
| Mature plant growth: indeterminate, determinate | Indeterminate | Indeterminate |
| Form: lax, open; normal; compact; dwarf; brachytic | Normal | Normal |
| Stem: | | |
| Branching: sparse, intermediate, profuse | Profuse | Profuse |
| Branching at cotyledonary or first leaf node: present, absent | Present | Present |
| No. of nodes between 1$^{st}$ inflorescence: few (1-4), several (5-9), many (10 or more) | Few | Several |
| No. of nodes between early (1$^{st}$-2$^{nd}$, 2$^{nd}$-3$^{rd}$) inflorescence: few (1-4), several (5-9), many (10 or more) | Few | Few |
| No. of nodes between later developing inflorescences: few (1-4), several (5-9), many (10 or more) | Few | Few |
| Leaf (mature leaf beneath the 3$^{rd}$ inflorescence) | | |
| Type of leaf blade: bipinnate, pinnate | Bipinnate | Bipinnate |
| Margin of major leaflets: nearly entire, shallowly toothed or scalloped, deeply toothed or cut toward base | Shallowly toothed or scalloped | Shallowly toothed or scalloped |
| Marginal rolling or wiltiness: absent, slight, moderate, strong | Absent | Absent |
| Surface of major leaflets: smooth, rugose (bumpy or veiny) | Smooth | Smooth |
| Pubescence: Smooth (no long hairs), normal, hirsute, wooly | Smooth | Smooth |
| Inflorescence (3$^{rd}$ inflorescence) | | |
| Type: simple, forked, compound | Simple | Simple |
| Average number of flowers in inflorescence: | 15.87 | 19.73 |
| Leafy or "running" inflorescence: absent, occasional, frequent | Occasional | Occasional |
| Flower: | | |
| Corolla color: yellow, old gold, white or tan | Yellow | Yellow |
| Style pubescence: absent, sparse, dense | Present | Present |
| Fruit (3$^{rd}$ fruit of 2$^{nd}$ or 3$^{rd}$ cluster): | | |
| Fruit shape: flattened, slightly flattened, round, high round, pear, lengthened-pear, plum or egg shape, heart, lengthened cylindrical, angular | Round | Round |
| Shape of transverse section: round, flattened, angular, irregular | Round | Round |
| Shape of blossom end: indented, flat, nippled, tapered | Flat | Flat |
| Shape of stem end: flat, indented | Indented | Flat |
| Shape of pistil scar: dot, stellate, linear, irregular | Dot | Dot |
| Abscission layer: Present (pedicellate), absent (jointless) | Present | Present |
| Point of detachment of fruit at harvest: at pedicel joint, at calyx attachment | At pedicel joint | At pedicel joint |

TABLE 2-continued

| Characteristics | Application Variety (NUN 09398 TOF) | Reference Variety (NUN 09231 TOF) |
|---|---|---|
| | Characteristics of Tomato Variety NUN 09398 TOF and the Reference Variety (USDA Descriptors) | |
| Length of pedicel from joint to calyx attachment, mm: | 7.82 mm | 7.54 mm |
| Length of mature stem axis, mm: | 193.64 mm | 203.94 mm |
| Diameter of fruit at widest point, mm: | 26.23 mm | 28.12 mm |
| Mature fruit weight, g: | 8.27 g | 11.33 g |
| Number of locules: two to three, three and four, five or more | Two | Two |
| Fruit surface: smooth, slightly rough, moderately rough or ribbed | Slightly rough | Slightly rough |
| Fruit base color at mature-green stage: light green, yellow green, apple or medium green, light gray-green, dark green | Medium green | Light green |
| Fruit pattern at mature-green stage: uniform green, green-shouldered, radial stripes on sides of fruit | Green-shouldered | Green-shouldered |
| Shoulder color if different from base: dark green, gray green, yellow green | Grey green | Grey green |
| Fruit color, full-ripe: white, yellow, orange, pink, red, brownish, greenish, red with purple, yellow with purple | Red RHS 175B | Red RHS 172A |
| Flesh color, full-ripe: yellow, red/crimson, pink, orange, brownish, greenish | Red RHS 173A | Red RHS 173A |
| Flesh color: uniform, with lighter and darker areas in walls | Uniform | Uniform |
| Locular gel color of table-ripe fruit: green, yellow, red | Red | Red |
| Stem scar size: small, medium, large | Small | Small |
| Fruit core: coreless, present | Coreless | Coreless |
| Epidermis color: colorless, yellow | Yellow | Coreless |
| Thickness of pericarp: thin, medium, thick | Thin | Thin |
| Adaptation: | | |
| Culture: field, greenhouse, both | Greenhouse | Greenhouse |
| Principle use(s): home garden, fresh market, whole pack canning, concentrated products, other | Fresh market | Fresh market |
| Resistances: | | |
| *Passalora fulva* Race 0 | Highly resistant | Highly resistant |
| *Passalora fulva* Group A | Highly resistant | Highly resistant |
| *Passalora fulva* Group B | Highly resistant | Highly resistant |
| *Passalora fulva* Group C | Highly resistant | Highly resistant |
| *Passalora fulva* Group D | Highly resistant | Highly resistant |
| *Passalora fulva* Group E | Highly resistant | Highly resistant |
| Tomato Mosaic Virus (ToMV) Strain 0 | Highly resistant | Highly resistant |
| Tomato Mosaic Virus (ToMV) Strain 1 | Highly resistant | Highly resistant |
| Tomato Mosaic Virus (ToMV) Strain 2 | Highly resistant | Highly resistant |
| Tomato Mosaic Virus (ToMV) Strain 1-2 | Highly resistant | Highly resistant |
| Tobacco Mosaic Virus | Present | Absent |
| Tomato Brown Rugose Fruit Virus (ToBRFV) | Intermediately resistant | Absent |

TABLE 3

| Characteristics | Application Variety (NUN 09398 TOF) | Reference Variety (NUN 09231 TOF) |
|---|---|---|
| Characteristics of Tomato Variety NUN 09398 TOF and the Reference Variety (Non-USDA Descriptors) | | |
| Mature plant (at maximum vegetative development): | | |
| No. of inflorescences on main stem (side shoots to be removed - only determinate growth type varieties): very few, very few to few, few, few to medium, medium, medium to many, many, many to very many, very many | Many | Many |
| Height (only indeterminate growth type varieties): very short, short, medium, long, very long | Medium to long | Medium to long |
| Stem: | | |
| Anthocyanin coloration of upper third: absent or very weak, weak, medium, strong, very strong | Absent or very weak | Very weak to weak |
| Length of internode (only indeterminate type growth varieties): short, medium, long | Short | Short |
| Number of nodes to $1^{st}$ inflorescence: | 3.93 | 5.80 |
| Number of nodes between $1^{st}$ and $2^{nd}$ inflorescence: | 3.33 | 3.73 |
| Number of nodes between $2^{nd}$ and $3^{rd}$ inflorescence: | 3.40 | 2.87 |
| $2^{nd}$ internode length, mm: | 24.50 mm | 25.75 mm |
| 3rd internode length, mm: | 27.68 mm | 32.63 mm |
| $4^{th}$ internode length, mm: | 31.84 mm | 34.97 mm |
| Leaf (mature leaf beneath the $3^{rd}$ inflorescence): | | |
| Attitude (in middle third of plant): semi-erect; horizontal; drooping | Horizontal to semi-drooping | Horizontal to semi-drooping |
| Length: very short, very short to short, short, short to medium, medium, medium to long, long, long to very long, very long | Medium | Medium |
| Width: very narrow, very narrow to narrow, narrow, narrow to medium, medium, medium to broad, broad, broad to very broad, very broad | Medium | Medium |
| Size of leaflets (in middle of leaf): very small, very small to small, small, small to medium, medium, medium to large, large to very large, very large | Medium to large | Medium to large |
| Intensity of green color: very light, very light to light, light, light to medium, medium, medium to dark, dark, dark to very dark, very dark | Medium to dark | Medium to dark |
| Glossiness (in middle third of plant): very weak, very weak to weak, weak, weak to medium, medium, medium to strong, strong, strong to very strong, very strong | Weak to medium | Weak to medium |
| Blistering (in middle third of plant): very weak, very weak to weak, weak, weak to medium, medium, medium to strong, strong, strong to very strong, very strong | Medium | Medium |
| Size of blisters (in middle third of plant): very small, very small to small, small, small to medium, medium, medium to large, large to very large, very large | Small | Small |
| Attitude of petiole leaflet in relation to main axis (in middle third of plant): erect, erect to semi-erect, semi-erect, semi-erect to horizontal, horizontal, horizontal to semi-drooping, semi-drooping, semi-drooping to drooping, drooping | Semi-erect to horizontal | Semi-erect to horizontal |
| Leaf structure: open, intermediate, closed | Intermediate | Intermediate |
| Color: light green, medium green, dark green | Medium green RHS N137B | Medium green RHS N137A |
| Anthocyanin coloration of nerves: absent, present | Absent | Absent |

TABLE 3-continued

Characteristics of Tomato Variety NUN 09398 TOF
and the Reference Variety (Non-USDA Descriptors)

| Characteristics | Application Variety (NUN 09398 TOF) | Reference Variety (NUN 09231 TOF) |
|---|---|---|
| Inflorescence: | | |
| Type (2$^{nd}$ and 3$^{rd}$ truss):<br>mainly uniparous, equally uniparous and<br>multiparous, mainly multiparous | Mainly uniparous | Mainly uniparous |
| Flower: | | |
| Color:<br>yellow, orange | Yellow | Yellow |
| Anther color:<br>green, yellow | Yellow | Yellow |
| Peduncle: | | |
| Length (from abscission layer to calyx):<br>very short, very short to short, short, short to<br>medium, medium, medium to long, long,<br>long to very long, very long | Short | Short |
| Peduncle length, mm: | 7.82 mm | 7.54 mm |
| Peduncle width, mm: | 2.32 mm | 2.47 mm |
| Fruit (3$^{rd}$ fruit of 2$^{nd}$ or 3$^{rd}$ cluster): | | |
| Green shoulder (before maturity):<br>absent, present | Present | Present |
| Extent of green shoulder (before maturity):<br>very small, very small to small, small to<br>medium, medium, medium to large, large,<br>large to very large, very large | Medium | Medium |
| Intensity of green color of shoulder (before<br>maturity):<br>very light, very light to light, light, light to<br>medium, medium, medium to dark, dark,<br>dark to very dark, very dark | Medium | Medium |
| Intensity of green color excluding shoulder<br>(before maturity):<br>very light, very light to light, light, light to<br>medium, medium, medium to dark, dark,<br>dark to very dark, very dark | Very light to light | Very light to light |
| Green stripes (before maturity):<br>absent, present | Absent | Absent |
| Size:<br>very small, very small to small, small to<br>medium, medium, medium to large, large,<br>large to very large, very large | Very small | Very small |
| Ratio length/width:<br>very compressed, moderately compressed,<br>medium, moderately elongated, very<br>elongated | Moderately compressed to medium | Medium |
| Ratio length/width: | 0.87 | 0.90 |
| Shape in longitudinal section:<br>flattened, oblate, circular, oblong,<br>cylindrical, elliptic, cordate, ovate, obovate,<br>pyriform, obcordate | Circular | Circular |
| Ribbing at peduncle end:<br>absent or very weak, very weak to weak,<br>weak, weak to medium, medium, medium to<br>strong, strong, strong to very strong, very<br>strong | Absent or very weak | Absent or very weak |
| Depression at peduncle end:<br>absent or very weak, very weak to weak,<br>weak, weak to medium, medium, medium to<br>strong, strong, strong to very strong, very<br>strong | Very weak to weak | Absent or very weak |
| Size of peduncle scar:<br>very small, very small to small, small to<br>medium, medium, medium to large, large,<br>large to very large, very large | Very small | Very small |
| Size of blossom scar:<br>very small, very small to small, small to<br>medium, medium, medium to large, large,<br>large to very large, very large | Very small | Very small |
| Shape of blossom end:<br>indented, indented, flat, flat to pointed,<br>conical | Flat | Flat |

TABLE 3-continued

Characteristics of Tomato Variety NUN 09398 TOF
and the Reference Variety (Non-USDA Descriptors)

| Characteristics | Application Variety (NUN 09398 TOF) | Reference Variety (NUN 09231 TOF) |
| --- | --- | --- |
| Diameter of core in cross-section in relation to total diameter: very small, very small to small, small to medium, medium, medium to large, large, large to very large, very large | Small to medium | Small |
| Thickness of pericarp, mm: | 2.01 mm | 2.08 mm |
| Cross-section: not round, round | Round | Round |
| Glossiness of skin: weak, medium, strong | Medium | Medium |
| Firmness: very soft, very soft to soft, soft, soft to medium, medium, medium to firm, firm, firm to very firm, very firm | Firm | Firm |
| Shelf life: very short, very short to short, short, short to medium, medium, medium to long, long, long to very long, very long | Long | Very long |
| Mature fruit length, mm: | 22.95 mm | 25.39 mm |
| Stem scar diameter, mm: | 3.28 mm | 3.56 mm |

TABLE 4

Distinguishing Characteristics between Tomato
Variety NUN 09398 TOF and the Reference Variety

| Characteristics | Application Variety (NUN 09398 TOF) | Reference Variety (NUN 3351 TO) |
| --- | --- | --- |
| Stem: | | |
| No. of nodes between 1$^{st}$ inflorescence: few (1-4), several (5-9), many (10 or more) | Few | Several |
| Anthocyanin coloration of upper third: absent or very weak, weak, medium, strong, very strong | Absent or very weak | Very weak to weak |
| 3rd internode length, mm: | 27.68 mm | 32.63 mm |
| 4$^{th}$ internode length, mm: | 31.84 mm | 34.97 mm |
| Leaf (mature leaf beneath the 3$^{rd}$ inflorescence): | | |
| Color: light green, medium green, dark green | Medium green RHS N137B | Medium green RHS N137A |
| Fruit (3$^{rd}$ fruit of 2$^{nd}$ or 3$^{rd}$ cluster): | | |
| Shape of stem end: flat, indented | Indented | Flat |
| Diameter of fruit at widest point, mm: | 26.23 mm | 28.12 mm |
| Mature fruit weight, g: | 8.27 g | 11.33 g |
| Fruit base color at mature-green stage: light green, yellow green, apple or medium green, light gray-green, dark green | Medium green | Light green |
| Fruit color, full-ripe: white, yellow, orange, pink, red, brownish, greenish, red with purple, yellow with purple | Red RHS 175B | Red RHS 172A |
| Epidermis color: colorless, yellow | Yellow | Coreless |
| Ratio length/width: very compressed, moderately compressed, medium, moderately elongated, very elongated | Moderately compressed to medium | Medium |
| Depression at peduncle end: absent or very weak, very weak to weak, weak, weak to medium, medium, medium to strong, strong, strong to very strong, very strong | Very weak to weak | Absent or very weak |
| Diameter of core in cross-section in relation to total diameter: very small, very small to small, small to medium, medium, medium to large, large, | Small to medium | Small |

TABLE 4-continued

Distinguishing Characteristics between Tomato
Variety NUN 09398 TOF and the Reference Variety

| Characteristics | Application Variety (NUN 09398 TOF) | Reference Variety (NUN 3351 TO) |
|---|---|---|
| large to very large, very large | | |
| Shelf life: | Long | Very long |
| very short, very short to short, short, short to medium, medium, medium to long, long, long to very long, very long | | |
| Mature fruit length, mm: | 22.95 mm | 25.39 mm |
| Disease Resistances: | | |
| Tobacco Mosaic Virus | Present | Absent |
| Tomato Brown Rugose Fruit Virus (ToBRFV) | Intermediately resistant | Absent |

The results of the T-test show significant differences at 5% significance level between tomato variety NUN 09398 TOF and the Reference Variety for $3^{rd}$ internode length, $4^{th}$ internode length, mature fruit diameter, mature fruit weight, and mature fruit length as shown in Tables 5-9.

Table 5 shows a significant difference at 5% significance level between tomato variety NUN 09398 TOF and the Reference Variety (p=0.002) on $3^{rd}$ internode length (mm) based on the results of the trial conducted in the US in 2022.

TABLE 5

| Statistical Parameters | Application Variety (NUN 09398 TOF) | Reference Variety (NUN 09231 TOF) |
|---|---|---|
| No. of samples | 15 | 15 |
| Minimum | 17.57 | 29.14 |
| Maximum | 35.51 | 39.15 |
| Median | 26.98 | 32.25 |
| Mean | 27.68 | 32.63 |
| Standard deviation | 4.67 | 2.88 |

Table 6 shows a significant difference at 5% significance level between tomato variety NUN 09398 TOF and the Reference Variety (p=0.031) on 4th internode length (mm) based on the results of the trial conducted in the US in 2022.

TABLE 6

| Statistical Parameters | Application Variety (NUN 09398 TOF) | Reference Variety (NUN 09231 TOF) |
|---|---|---|
| No. of samples | 15 | 15 |
| Minimum | 23.57 | 23.37 |
| Maximum | 36.87 | 39.68 |
| Median | 32.49 | 35.64 |
| Mean | 31.84 | 34.97 |
| Standard deviation | 3.56 | 3.97 |

Table 7 shows a significant difference at 5% significance level between tomato variety NUN 09398 TOF and the Reference Variety (p<0.001) on mature fruit weight (g) based on the results of the trial conducted in the US in 2022.

TABLE 7

| Statistical Parameters | Application Variety (NUN 09398 TOF) | Reference Variety (NUN 09231 TOF) |
|---|---|---|
| No. of samples | 15 | 15 |
| Minimum | 4.0 | 8.0 |
| Maximum | 12.0 | 14.0 |
| Median | 8.0 | 12.0 |

TABLE 7-continued

| Statistical Parameters | Application Variety (NUN 09398 TOF) | Reference Variety (NUN 09231 TOF) |
|---|---|---|
| Mean | 8.27 | 11.33 |
| Standard deviation | 1.98 | 1.98 |

Table 8 shows a significant difference at 5% significance level between tomato variety NUN 09398 TOF and the Reference Variety (p<0.001) on mature fruit diameter (mm) based on the results of the trial conducted in the US in 2022.

TABLE 8

| Statistical Parameters | Application Variety (NUN 09398 TOF) | Reference Variety (NUN 09231 TOF) |
|---|---|---|
| No. of samples | 15 | 15 |
| Minimum | 24.89 | 24.59 |
| Maximum | 27.95 | 29.86 |
| Median | 26.18 | 28.69 |
| Mean | 26.23 | 28.12 |
| Standard deviation | 0.88 | 1.51 |

Table 9 shows a significant difference at 5% significance level between tomato variety NUN 09398 TOF and the Reference Variety (p<0.001) on mature fruit length (mm) based on the results of the trial conducted in the US in 2022.

TABLE 9

| Statistical Parameters | Application Variety (NUN 09398 TOF) | Reference Variety (NUN 09231 TOF) |
|---|---|---|
| No. of samples | 15 | 15 |
| Minimum | 22.07 | 22.91 |
| Maximum | 24.31 | 27.23 |
| Median | 22.64 | 26.09 |
| Mean | 22.95 | 25.39 |
| Standard deviation | 0.70 | 1.47 |

The results of the T-test show no significant differences at 5% significance level between tomato variety NUN 09398 TOF and the Reference Variety for $2^{nd}$ internode length, length of mature fruit stem axis, peduncle length, peduncle width, thickness of pericarp, and stem scar diameter as shown in Tables 10-15.

Table 10 shows no significant difference at 5% significance level between tomato variety NUN 09398 TOF and the Reference Variety (p=0.437) on $2^{nd}$ internode length (mm) based on the results of the trial conducted in the US in 2022.

TABLE 10

| Statistical Parameters | Application Variety (NUN 09398 TOF) | Reference Variety (NUN 09231 TOF) |
|---|---|---|
| No. of samples | 15 | 15 |
| Minimum | 18.37 | 15.99 |
| Maximum | 31.50 | 36.09 |
| Median | 24.20 | 25.21 |
| Mean | 24.50 | 25.75 |
| Standard deviation | 3.76 | 4.86 |

Table 11 shows no significant difference at 5% significance level between tomato variety NUN 09398 TOF and the Reference Variety (p=0.474) on length of mature fruit axis (mm) based on the results of the trial conducted in the US in 2022.

TABLE 11

| Statistical Parameters | Application Variety (NUN 09398 TOF) | Reference Variety (NUN 09231 TOF) |
|---|---|---|
| No. of samples | 15 | 15 |
| Minimum | 144.61 | 145.78 |
| Maximum | 261.24 | 285.53 |
| Median | 189.29 | 210.34 |
| Mean | 193.64 | 203.94 |
| Standard deviation | 33.31 | 43.68 |

Table 12 shows no significant difference at 5% significance level between tomato variety NUN 09398 TOF and the Reference Variety (p=0.208) on peduncle length (mm) based on the results of the trial conducted in the US in 2022.

TABLE 12

| Statistical Parameters | Application Variety (NUN 09398 TOF) | Reference Variety (NUN 09231 TOF) |
|---|---|---|
| No. of samples | 15 | 15 |
| Minimum | 6.58 | 6.31 |
| Maximum | 8.72 | 8.26 |
| Median | 7.87 | 7.65 |
| Mean | 7.82 | 7.54 |
| Standard deviation | 0.66 | 0.53 |

Table 13 shows no significant difference at 5% significance level between tomato variety NUN 09398 TOF and the Reference Variety (p=0.329) on peduncle width (mm) based on the results of the trial conducted in the US in 2022.

TABLE 13

| Statistical Parameters | Application Variety (NUN 09398 TOF) | Reference Variety (NUN 09231 TOF) |
|---|---|---|
| No. of samples | 15 | 15 |
| Minimum | 2.07 | 1.91 |
| Maximum | 3.27 | 3.58 |
| Median | 7.87 | 2.27 |
| Mean | 7.82 | 2.47 |
| Standard deviation | 0.66 | 0.51 |

Table 14 shows no significant difference at 5% significance level between tomato variety NUN 09398 TOF and the Reference Variety (p=0.486) on thickness of pericarp (mm) based on the results of the trial conducted in the US in 2022.

TABLE 14

| Statistical Parameters | Application Variety (NUN 09398 TOF) | Reference Variety (NUN 09231 TOF) |
|---|---|---|
| No. of samples | 15 | 15 |
| Minimum | 1.48 | 1.64 |
| Maximum | 2.75 | 2.44 |
| Median | 1.94 | 2.09 |
| Mean | 2.01 | 2.08 |
| Standard deviation | 0.30 | 0.26 |

Table 15 shows no significant difference at 5% significance level between tomato variety NUN 09398 TOF and the Reference Variety (p=0.079) on stem scar diameter (mm) based on the results of the trial conducted in the US in 2022.

TABLE 15

| Statistical Parameters | Application Variety (NUN 09398 TOF) | Reference Variety (NUN 09231 TOF) |
|---|---|---|
| No. of samples | 15 | 15 |
| Minimum | 2.55 | 2.95 |
| Maximum | 3.90 | 4.38 |
| Median | 3.22 | 3.47 |
| Mean | 3.28 | 3.56 |
| Standard deviation | 0.37 | 0.46 |

The invention claimed is:

1. A plant or seed of tomato variety NUN 09398 TOF, wherein a representative sample of seed of said tomato variety NUN 09398 TOF has been deposited under Accession Number NCIMB 44028.

2. A plant part of the plant of claim 1, wherein said plant part is a fruit, a leaf, a pollen, an ovule, a cell, a scion, a root, a rootstock, a cutting, or a flower.

3. A seed that produces the plant of claim 1.

4. A plant produced by growing the seed of claim 1.

5. A tomato plant or part thereof having all the physiological and morphological characteristics of the plant of claim 1 when grown under the same environmental conditions.

6. A tissue culture or cell culture of regenerable cells of the plant of claim 1 or plant part thereof, wherein said cells are obtained from tomato variety NUN 09398 TOF and are suitable for regeneration into a plant having all of the physiological and morphological characteristics of tomato variety NUN 09398 TOF.

7. The tissue or cell culture according to claim 6, comprising cells or protoplasts obtained from a plant part suitable for vegetative reproduction, wherein the plant part is a meristem, a cotyledon, a hypocotyl, a pollen, a leaf, an anther, a root, a root tip, a pistil, a petiole, a flower, a fruit, a stem, or a stalk.

8. A method of producing the plant of claim 1 or a part thereof, said method comprising vegetative propagation of at least a part of the plant of tomato variety NUN 09398 TOF, wherein a representative sample of seed of said tomato variety has been deposited under Accession Number NCIMB 44028.

9. The method of claim 8, wherein said part is a cutting, a cell culture, or a tissue culture.

10. A vegetatively propagated plant, or a part thereof, produced by the method of claim 8, wherein the plant or a part thereof has all of the physiological and morphological characteristics of the plant of tomato variety NUN 09398 TOF when grown under the same environmental conditions, and wherein a representative sample of seed of said tomato variety NUN 09398 TOF has been deposited under Accession Number NCIMB 44028.

11. A method of producing a tomato plant, said method comprising crossing the plant of claim 1 with a second tomato plant at least once, producing a progeny tomato plant from said crossing, and optionally allowing the progeny tomato plant to form seed.

12. A method of making doubled haploids of the plant of claim 1, said method comprising making double haploid cells from haploid cells of the plant or plant part of tomato variety NUN 09398 TOF, wherein a representative sample of seed of said tomato variety NUN 09231 TOF has been deposited under Accession Number NCIMB 44028.

13. A plant comprising the scion or rootstock of claim 2.

14. A container comprising the plant or seed of claim 1.

15. A food, a feed, or a processed product comprising the plant part of claim 2, wherein the plant part comprises at least a regenerable cell of tomato variety NUN 09398 TOF.

16. A method of introducing a desired trait into the plant of claim 1, wherein said method comprises transforming the plant of claim 1 with a transgene that confers the desired trait, wherein the desired trait is male sterility, herbicide tolerance, insect resistance, pest resistance, disease resistance, environmental stress tolerance, modified carbohydrate metabolism, or modified protein metabolism.

17. A tomato plant produced by the method of claim 16, wherein the transformed plant comprises the desired trait and otherwise has all the physiological and morphological characteristics of tomato variety NUN 09398 TOF.

18. A method of producing a tomato fruit, said method comprising growing the plant of claim 1 until it sets at least one fruit, and collecting the fruit.

19. A fruit produced by the method of claim 18.

20. A container comprising the tomato fruit collected by the method of claim 18.

21. A method of producing a modified tomato plant having a desired trait, wherein said method comprises mutating a plant or plant part of tomato variety NUN 09398 TOF and selecting the plant with the desired trait, wherein a representative ample of seed of said tomato variety has been deposited under Accession Number NCIMB 44028.

22. A tomato plant produced by the method of claim 21, wherein the modified plant comprises the desired trait and otherwise all the physiological and morphological characteristics of tomato variety NUN 09398 TOF and wherein the desired trait is male sterility, herbicide tolerance, insect resistance, pest resistance, disease resistance, environmental stress tolerance, modified carbohydrate metabolism, or modified protein metabolism.

23. A method of producing a tomato seed, wherein said method comprises crossing tomato plants and harvesting the resultant seed, wherein at least one tomato plant in the cross is the plant of claim 1, wherein a representative sample of seed of said tomato variety NUN 09398 TOF has been deposited under Accession Number NCIMB 44028.

24. A method of introducing a single locus conversion into the plant of claim 1, comprising:
  a. crossing the plant of claim 1 with a second tomato plant comprising a desired single locus conversion to produce F1 progeny plants;
  b. selecting the F1 progeny plants that have the single locus conversion to produce selected F1 progeny plants;

c. crossing selected F1 progeny plants with tomato variety NUN 09398 TOF to produce backcross progeny plants;
  d. selecting backcross progeny plants that have the single locus conversion and otherwise comprise all of the physiological and morphological characteristics of tomato variety NUN 09398 TOF to produce selected backcross progeny plants; and
  e. repeating steps (c) and (d) one or more times in succession to produce selected second or higher backcross progeny plants that comprise the single locus conversion and otherwise comprise all of the physiological and morphological characteristics of tomato variety NUN 09398 TOF, wherein a representative sample of seed of said tomato variety has been deposited under Accession Number NCIMB 44028.

25. A tomato plant produced by the method of claim 24, wherein the plant comprises the single locus conversion and otherwise has all the physiological and morphological characteristics of tomato variety NUN 09398 TOF, and wherein the single locus conversion confers male sterility, herbicide tolerance, insect resistance, pest resistance, disease resistance, environmental stress tolerance, modified carbohydrate metabolism, or modified protein metabolism.

26. A method of producing a tomato plant derived from the plant of claim 1, comprising:
  a. producing a progeny tomato plant from tomato variety NUN 09398 TOF by crossing the plant of claim 1 with itself or with a second tomato plant;
  b. crossing the progeny plant with itself or a different tomato plant to produce a seed of a progeny plant of the subsequent generation;
  c. growing a progeny plant of the subsequent generation from said seed and crossing the progeny plant of the subsequent generation with itself or another tomato plant; and
  d. repeating steps (b) and (c) for at least one more generation to produce a tomato plant derived from tomato variety NUN 09398 TOF.

27. A method of determining the genotype of the plant of claim 1, said method comprises obtaining a sample of nucleic acids from said plant, detecting in said nucleic acids a plurality of polymorphisms, thereby determining the genotype of the plant, and storing the results of detecting the plurality of polymorphisms on a computer readable medium.

28. A method of developing a tomato plant in a tomato breeding program, said method comprising applying plant breeding techniques comprising recurrent selection, backcrossing, pedigree breeding, mass selection, mutation breeding, genetic marker enhanced selection, or genetic transformation to the plant of claim 1 or part thereof.

29. A method of producing a modified tomato plant, wherein said method comprises mutating a target gene by targeted gene editing in a tomato plant or part thereof of tomato variety NUN 09398 TOF, wherein the target gene modifies a desired trait and wherein the desired trait is male sterility, herbicide tolerance, insect resistance, pest resistance, disease resistance, environmental stress tolerance, modified carbohydrate metabolism, or modified protein metabolism.

30. A modified tomato plant produced by the method of claim 29, comprising the mutated target gene and otherwise has all the physiological and morphological characteristics of tomato variety NUN 09398 TOF.

* * * * *